(12) United States Patent
Sheffer

(10) Patent No.: US 8,439,932 B2
(45) Date of Patent: May 14, 2013

(54) SUBMUSCULAR PLATING SYSTEM

(75) Inventor: Garrett A. Sheffer, Hoboken, NJ (US)

(73) Assignee: Biomet Manufacturing Corp., Warsaw, IN (US)

( * ) Notice: Subject to any disclaimer, the term of this patent is extended or adjusted under 35 U.S.C. 154(b) by 218 days.

(21) Appl. No.: 12/772,857

(22) Filed: May 3, 2010

(65) Prior Publication Data

US 2011/0270319 A1 Nov. 3, 2011

(51) Int. Cl.
*A61B 17/58* (2006.01)
*A61B 17/60* (2006.01)
*A61F 2/00* (2006.01)

(52) U.S. Cl.
USPC ........... 606/104; 606/86 B; 606/86 R; 606/96

(58) Field of Classification Search ................ 606/86 B, 606/86 R, 104, 101, 96–99, 280–299, 70, 606/71
See application file for complete search history.

(56) References Cited

U.S. PATENT DOCUMENTS

| | | |
|---|---|---|
| 1,007,107 A | 10/1911 | Hulsmann |
| 2,440,123 A | 4/1948 | Smith |
| 4,429,600 A | 2/1984 | Gulistan |
| 4,466,314 A | 8/1984 | Rich |
| 4,791,918 A | 12/1988 | Von Hasselbach |
| 5,042,983 A | 8/1991 | Rayhack |
| 5,207,682 A | 5/1993 | Cripe |
| 5,222,951 A | 6/1993 | Abidin et al. |
| 5,250,063 A | 10/1993 | Abidin et al. |
| 5,364,399 A | 11/1994 | Lowery et al. |
| 5,423,826 A | 6/1995 | Coates et al. |
| 5,429,641 A | 7/1995 | Gotfried |
| 5,524,879 A | 6/1996 | Lyle |
| 5,987,557 A | 11/1999 | Ebrahim |
| 6,066,174 A | 5/2000 | Farris |
| 6,077,267 A | 6/2000 | Huene |
| 6,260,452 B1 | 7/2001 | Yu |
| 6,319,257 B1 | 11/2001 | Carignan et al. |
| 6,436,103 B1 | 8/2002 | Suddaby |
| 6,565,573 B1 | 5/2003 | Ferrante et al. |
| 6,916,323 B2 | 7/2005 | Kitchens |
| 6,926,720 B2 | 8/2005 | Castaneda |
| 7,112,063 B2 | 9/2006 | Bulard et al. |
| 7,135,023 B2 | 11/2006 | Watkins et al. |
| 7,166,111 B2 | 1/2007 | Kolb et al. |
| 7,249,949 B2 | 7/2007 | Carter |
| 7,325,470 B2 | 2/2008 | Kay et al. |
| 7,404,795 B2 | 7/2008 | Ralph et al. |
| 7,431,731 B2 * | 10/2008 | Kitchens ....................... 606/281 |
| 7,473,255 B2 | 1/2009 | McGarity et al. |

(Continued)

*Primary Examiner* — Kevin T Truong
*Assistant Examiner* — Si Ming Lee
(74) *Attorney, Agent, or Firm* — Harness, Dickey

(57) ABSTRACT

The present teachings provide one or more surgical implements for repairing damaged tissue, such as in the case of a fixation procedure. For example, a system is provided that includes a bone plate having a first plurality of apertures and a targeting arm having a second plurality of apertures. Each of the second plurality of apertures of the targeting arm are configured for targeting of a bone fastener to one of first plurality of apertures. An imaginary targeting line extends from a first aperture of the first plurality of apertures to a first aperture of the second plurality of apertures. The system includes a mounting member, which includes a first end secured to the bone plate and a second end secured to the targeting arm. The second end of the mounting member is offset from the first end such that the second end is spaced from the imaginary targeting line.

24 Claims, 24 Drawing Sheets

U.S. PATENT DOCUMENTS

| | | |
|---|---|---|
| 2005/0085824 A1* | 4/2005 | Castaneda ............... 606/98 |
| 2005/0159747 A1 | 7/2005 | Orbay |
| 2005/0234472 A1 | 10/2005 | Huebner |
| 2006/0095044 A1* | 5/2006 | Grady et al. ............ 606/96 |
| 2006/0116679 A1* | 6/2006 | Lutz et al. ............... 606/69 |
| 2006/0200157 A1* | 9/2006 | Orbay et al. ............. 606/87 |
| 2007/0043367 A1 | 2/2007 | Lawrie |
| 2007/0173843 A1 | 7/2007 | Matityahu |
| 2007/0213726 A1* | 9/2007 | McGarity et al. ......... 606/69 |
| 2007/0276401 A1* | 11/2007 | Choe et al. ............. 606/96 |
| 2008/0027458 A1 | 1/2008 | Aikins et al. |
| 2008/0154312 A1 | 6/2008 | Colleran et al. |
| 2009/0005822 A1 | 1/2009 | Kitchens |
| 2009/0076554 A1 | 3/2009 | Huebner et al. |
| 2009/0076556 A1 | 3/2009 | McGarity et al. |
| 2009/0088767 A1* | 4/2009 | Leyden et al. ........... 606/96 |

* cited by examiner

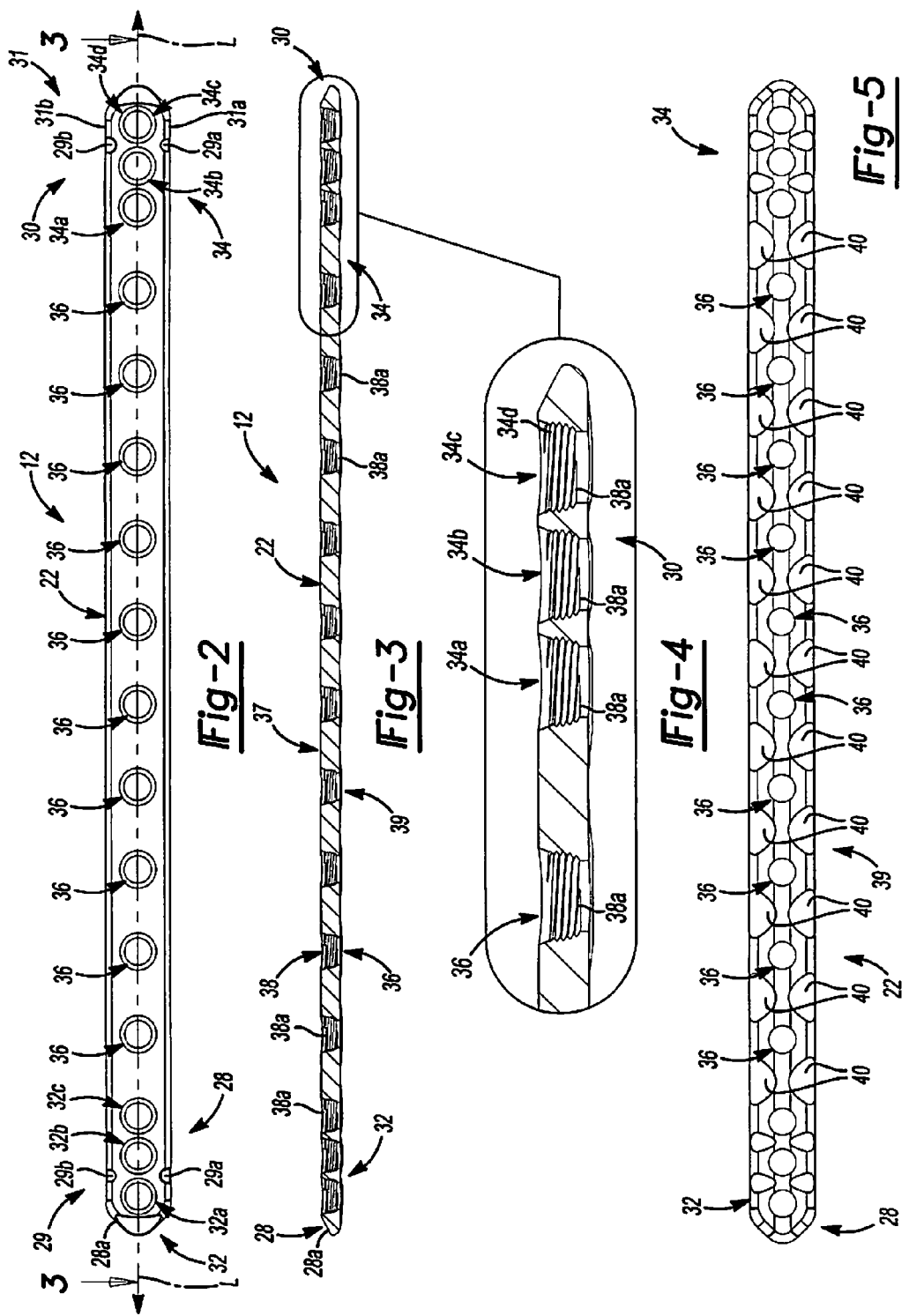

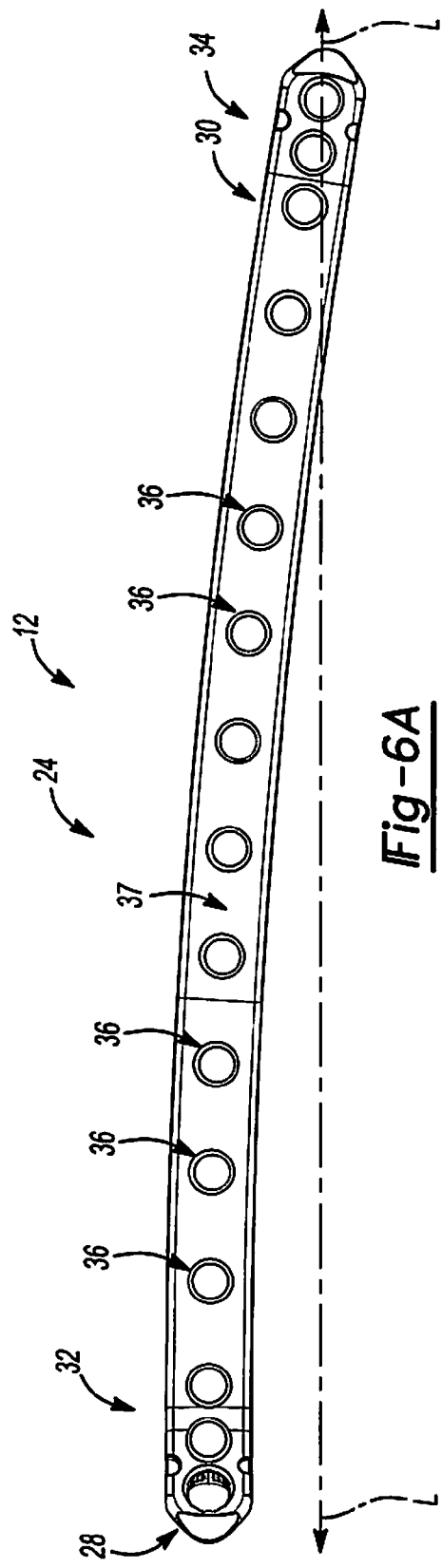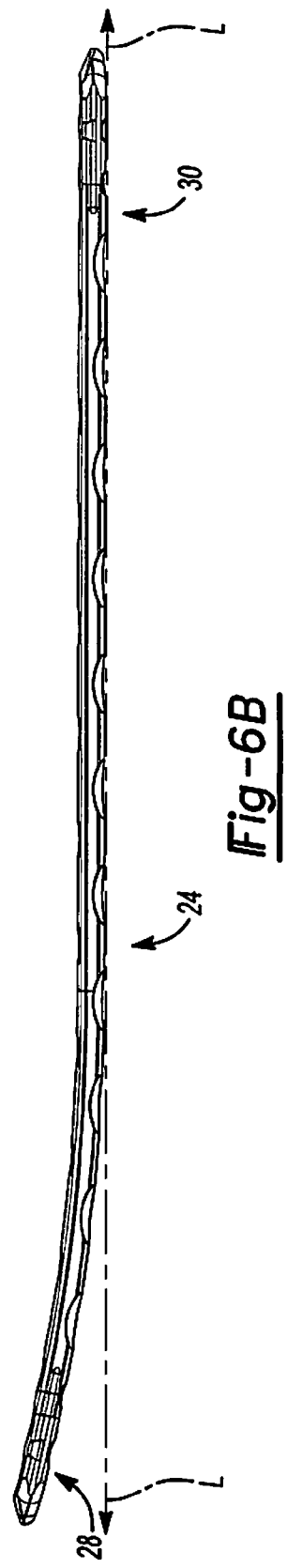

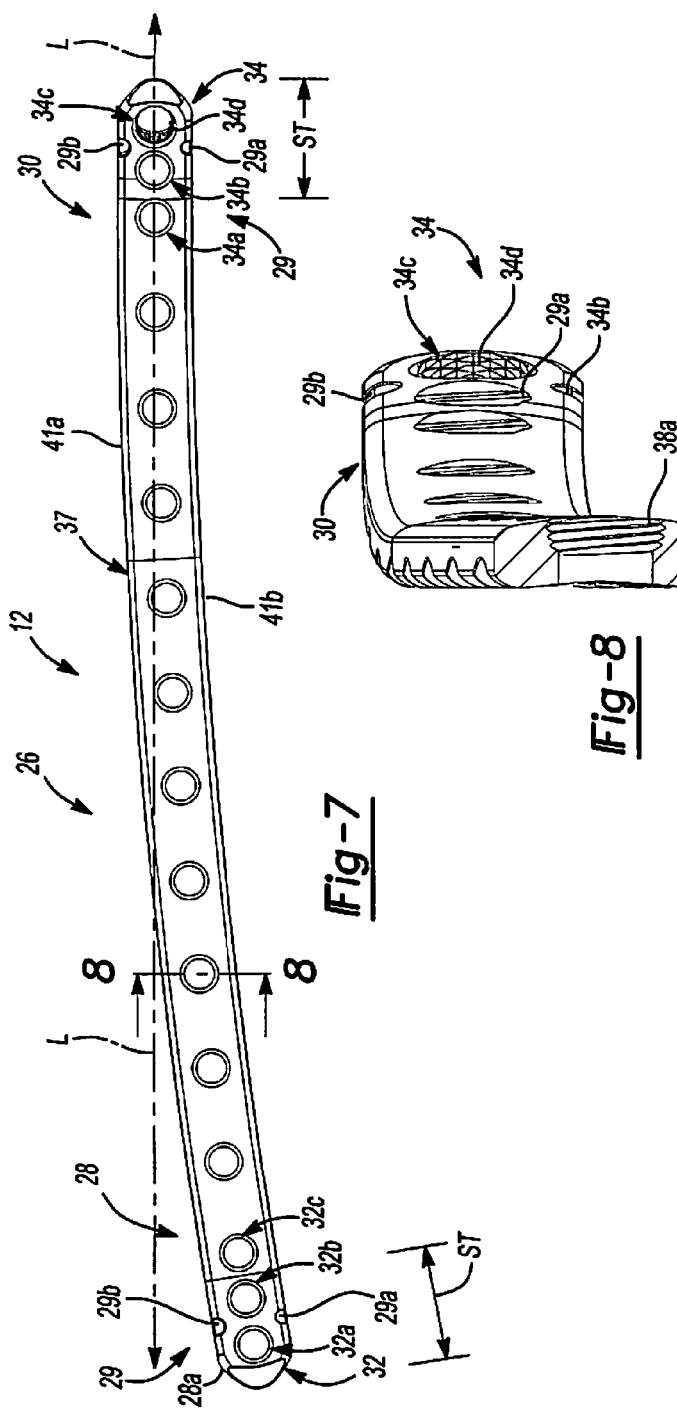
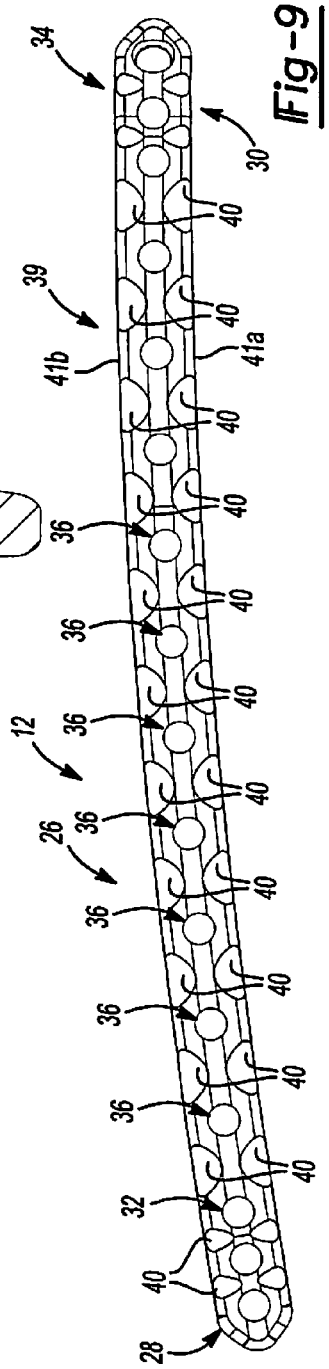

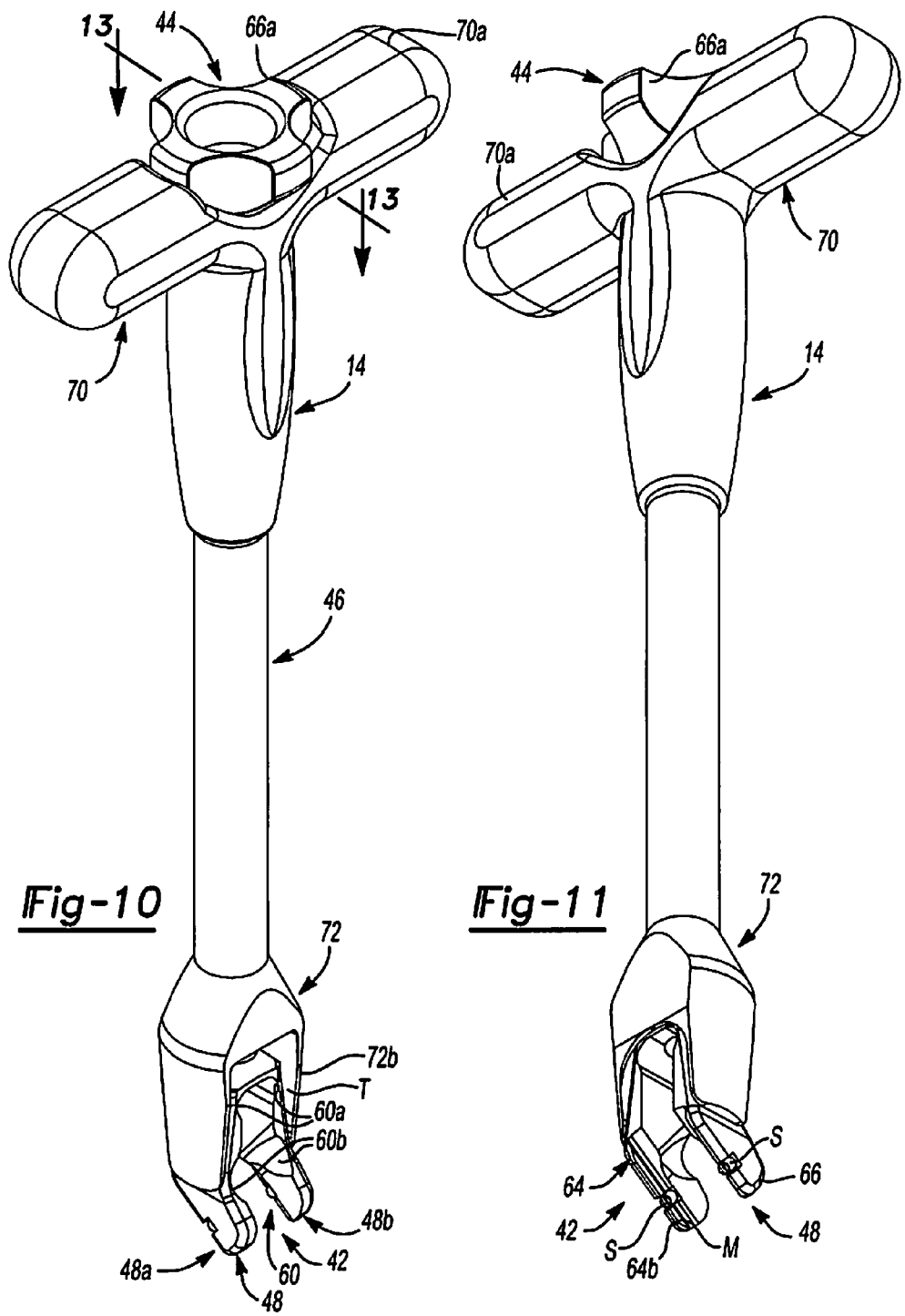

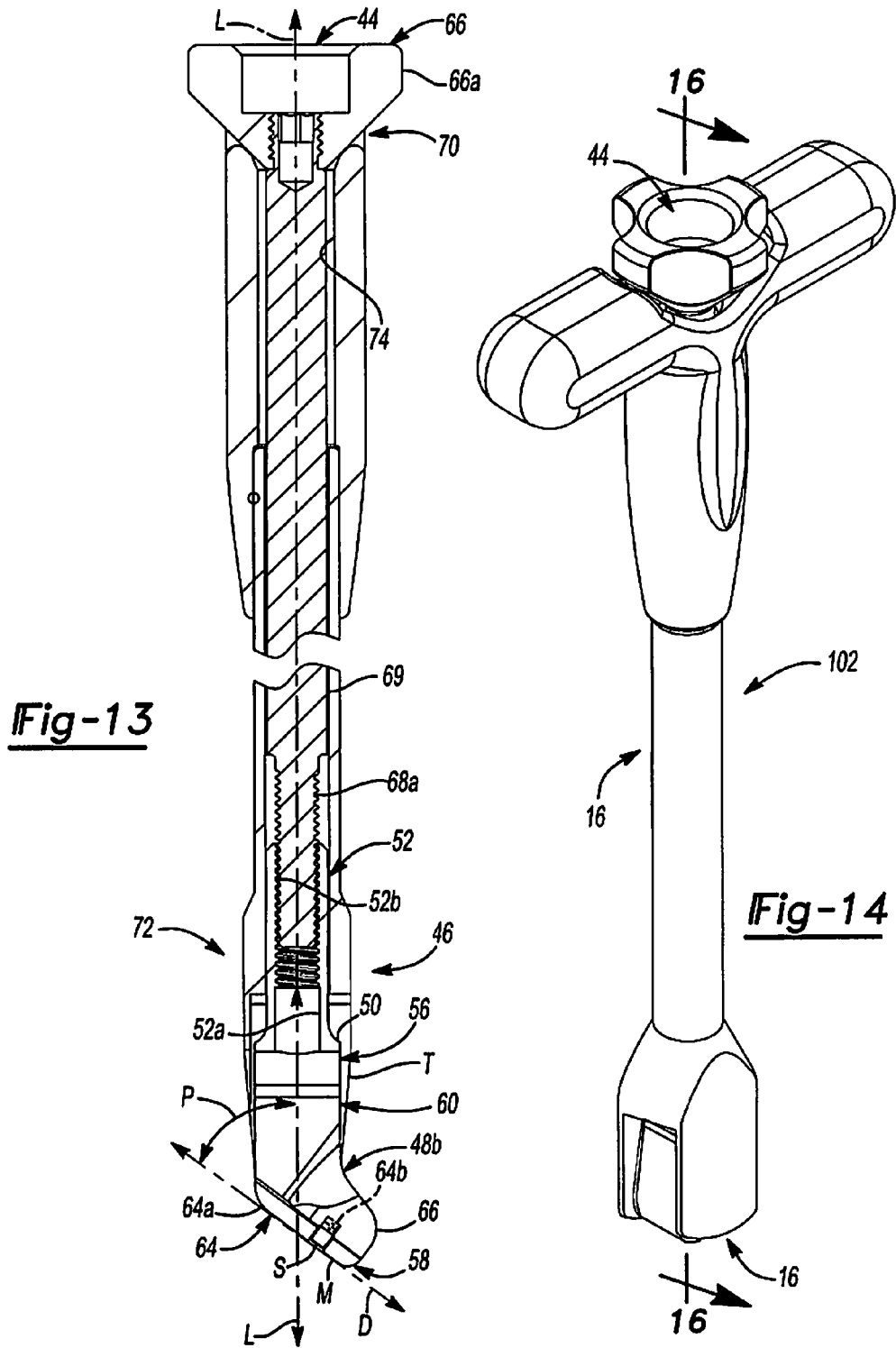

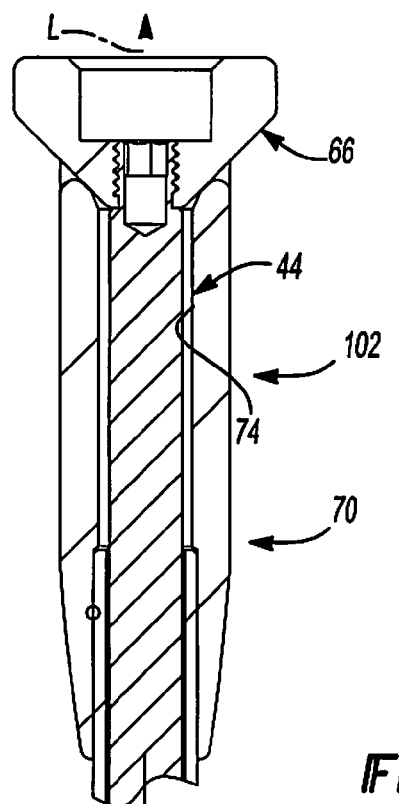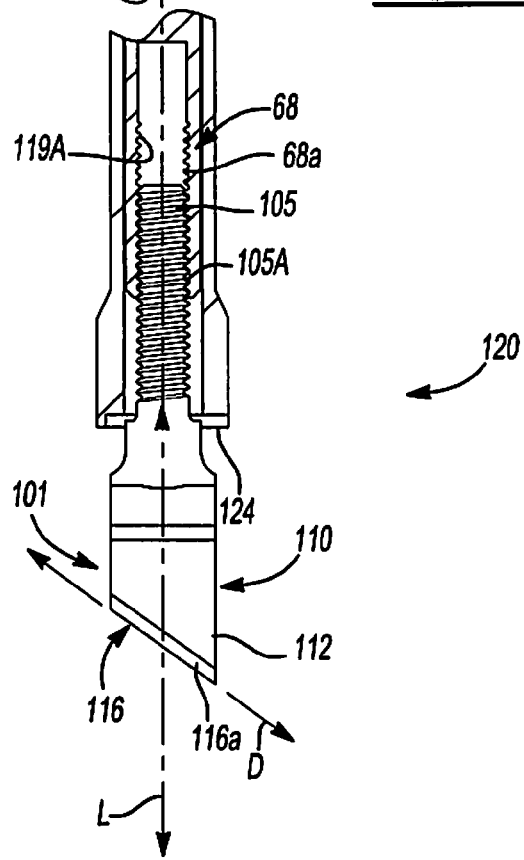
Fig-16

SUBMUSCULAR PLATING SYSTEM

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic prosthesis, such as orthopedic nails, screws, implants, etc., to restore function to the damaged tissue.

Generally, in order to stabilize various boney tissue relative to one another, such as in a fracture of a femur, the fractured portions of the femur can be interconnected via a suitable device. In one example, implants such as bone fasteners can be coupled to each bone fragment, and a connecting device, such as a plate, can interconnect each of the bone fasteners to stabilize or fix the bone fragments relative to each other. The present teachings can provide a system for use in repairing damaged tissue, such as a submuscular plating system for use in a fixation procedure.

Provided is an orthopedic fixation system for repairing a damaged portion of the anatomy. The system can include a bone plate having a first plurality of apertures passing therethrough. Each aperture of the first plurality of apertures can be adapted to receive a bone fastener. The system can also include a targeting arm having a second plurality of apertures passing therethrough. Each of the second plurality of apertures of the targeting arm can be configured and arranged for targeting of the bone fastener to a select one of first plurality of apertures. An imaginary targeting line can extend from a first aperture of the first plurality of apertures to a first aperture of the second plurality of apertures. The system can include a mounting member for mounting the targeting arm relative to the bone plate. The mounting member can include a first end secured to the bone plate and a second end secured to the targeting arm. The first end can include a forked element having first and second members positioned on laterally opposing sides of the first aperture of the first plurality of apertures such that the first aperture of the first plurality of apertures is positioned between the first and second members. The second end of the mounting member can be offset from the first end such that the second end is spaced from the imaginary targeting line.

Further provided is an orthopedic fixation system, which can include a bone plate having a first plurality of apertures passing therethrough. Each aperture of the first plurality of apertures of the bone plate can be adapted to receive a bone fastener. The system can also include a targeting arm having a second plurality of apertures passing therethrough. Each of the second plurality of apertures can be configured and arranged for targeting of the bone fastener to a select one of first plurality of apertures. The system can include a mounting member for mounting the targeting arm relative to the bone plate. The mounting member can include a first end movable between a first position in which the mounting member is movable relative to the bone plate and a second position in which the mounting member is secured to the bone plate. The mounting member can also include a second end having a platform for supporting the targeting arm relative to the bone plate, and an actuation member rotatably coupled to the mounting member between the platform and the first end. The actuation member can be rotatable to move the first end between the first position and the second position. The second end of the mounting member can be offset from the first end of the mounting member to provide access to each aperture of the plurality of apertures when the first end is in the second position.

Also provided is an orthopedic fixation system for repairing a damaged portion of the anatomy. The system can include a bone plate having a first plurality of apertures passing therethrough, with each aperture of the plurality of apertures adapted to receive a bone fastener. The system can also include a targeting arm having a second plurality of apertures passing therethrough, with each of the second plurality of apertures configured and arranged for targeting of the bone fastener to a select one of first plurality of apertures. An imaginary targeting line can extend from a first aperture of the first plurality of apertures to a first aperture of the second plurality of apertures. The system can include a mounting member for mounting the targeting arm relative to the bone plate. The mounting member can include a first end having a housing and a forked element. The housing can be movable relative to the forked element to secure the forked element to the bone plate. The mounting member can also include a second end having a platform for supporting the targeting arm relative to the bone plate, and an actuation member coupled to the housing and rotatably coupled to the mounting member between the platform and the forked member. The actuation member can be rotatable to move the housing relative to the forked element to secure the mounting member to the plate. The second end of the mounting member can be offset from the first end of the mounting member such that the second end is spaced from the imaginary targeting line.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 2 is a top view of an exemplary bone plate for use with the system of FIG. 1;

FIG. 3 is a cross-sectional view of the bone plate of FIG. 2, taken along line 3-3 of FIG. 2;

FIG. 4 is a detail view of a portion of the bone plate of FIG. 3;

FIG. 5 is a back view of the bone plate of FIG. 2;

FIG. 6A is a top view of the bone plate of FIG. 6;

FIG. 6B is a side view of the bone plate of FIG. 6;

FIG. 7 is a top view of another exemplary bone plate for use with the system of FIG. 1;

FIG. 8 is a cross-sectional view of the bone plate of FIG. 7, taken along line 8-8 of FIG. 7;

FIG. 9 is a back view of the bone plate of FIG. 7;

FIG. 10 is a perspective view of an exemplary plate mounting member for use with the system of FIG. 1;

FIG. 11 is a rear perspective view of the plate mounting member of FIG. 10;

FIG. 13 is a cross-sectional view of the plate mounting member of FIG. 10, taken along line 13-13 of FIG. 10;

FIG. 14 is a perspective view of another exemplary plate mounting member for use with the system of FIG. 1;

FIG. 16 is a cross-sectional view of the plate mounting member of FIG. 14, taken along line 16-16 of FIG. 14;

FIG. 21A is a perspective view of an exemplary modular target platform for use with the targeting arm of FIGS. 20 and 21;

DESCRIPTION OF VARIOUS ASPECTS

Figure 1:
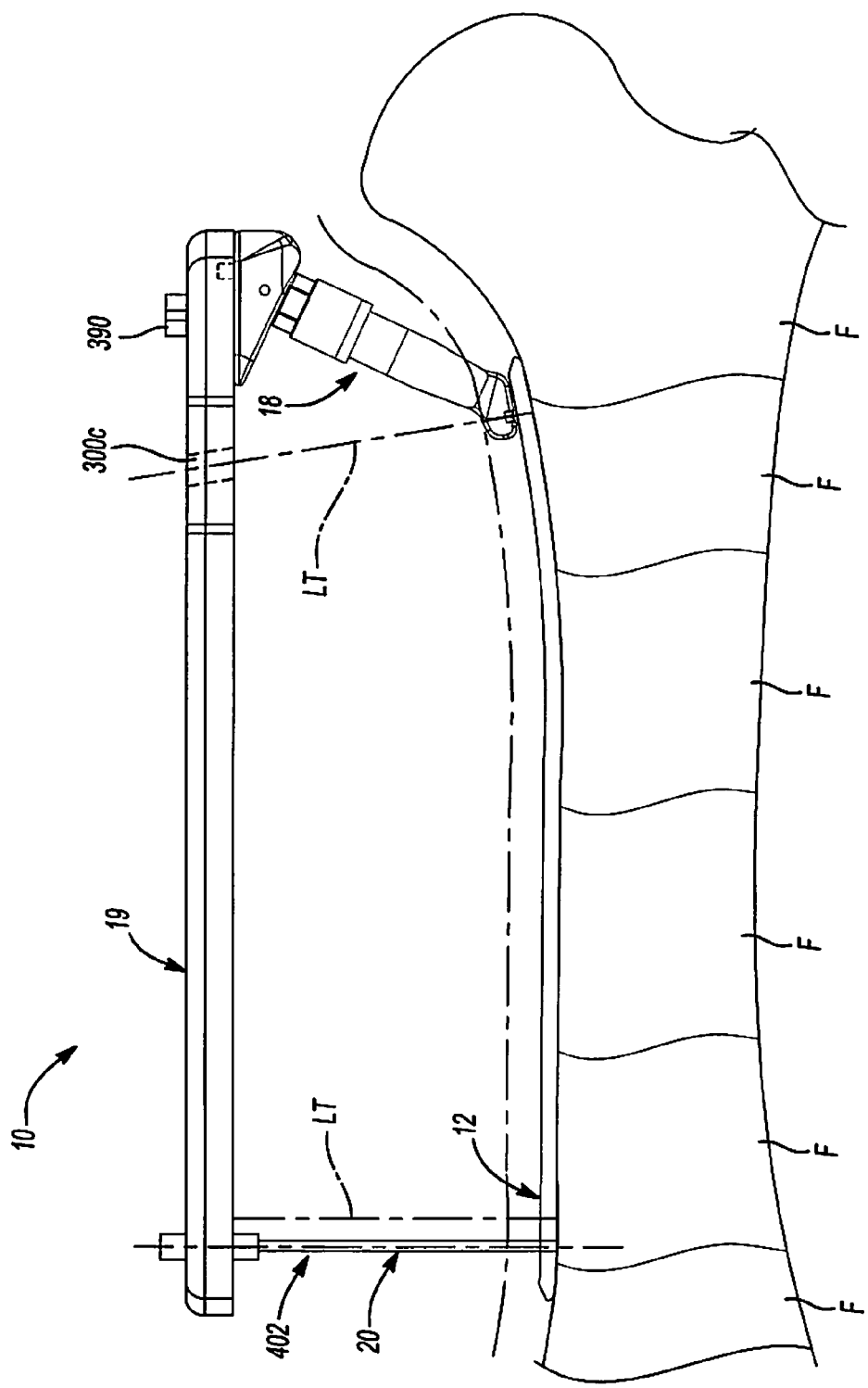
FIG. 1 is a schematic environmental illustration of an exemplary submuscular plating system for use in a fixation procedure according to the present teachings.

The following description is merely exemplary in nature and is not intended to limit the present teachings, application, or uses. It should be understood that throughout the drawings, corresponding reference numerals indicate like or corresponding parts and features. Although the following description is related generally to a system for use in an anatomy to repair damaged tissue, such as in the case of fractured long bone, for example, a femur, it will be understood that the system as described and claimed herein can be used in any appropriate surgical procedure, such as in a minimally invasive orthopedic alignment or fixation procedure. Therefore, it will be understood that the following discussions are not intended to limit the scope of the present teachings and claims herein.

Figure 22:
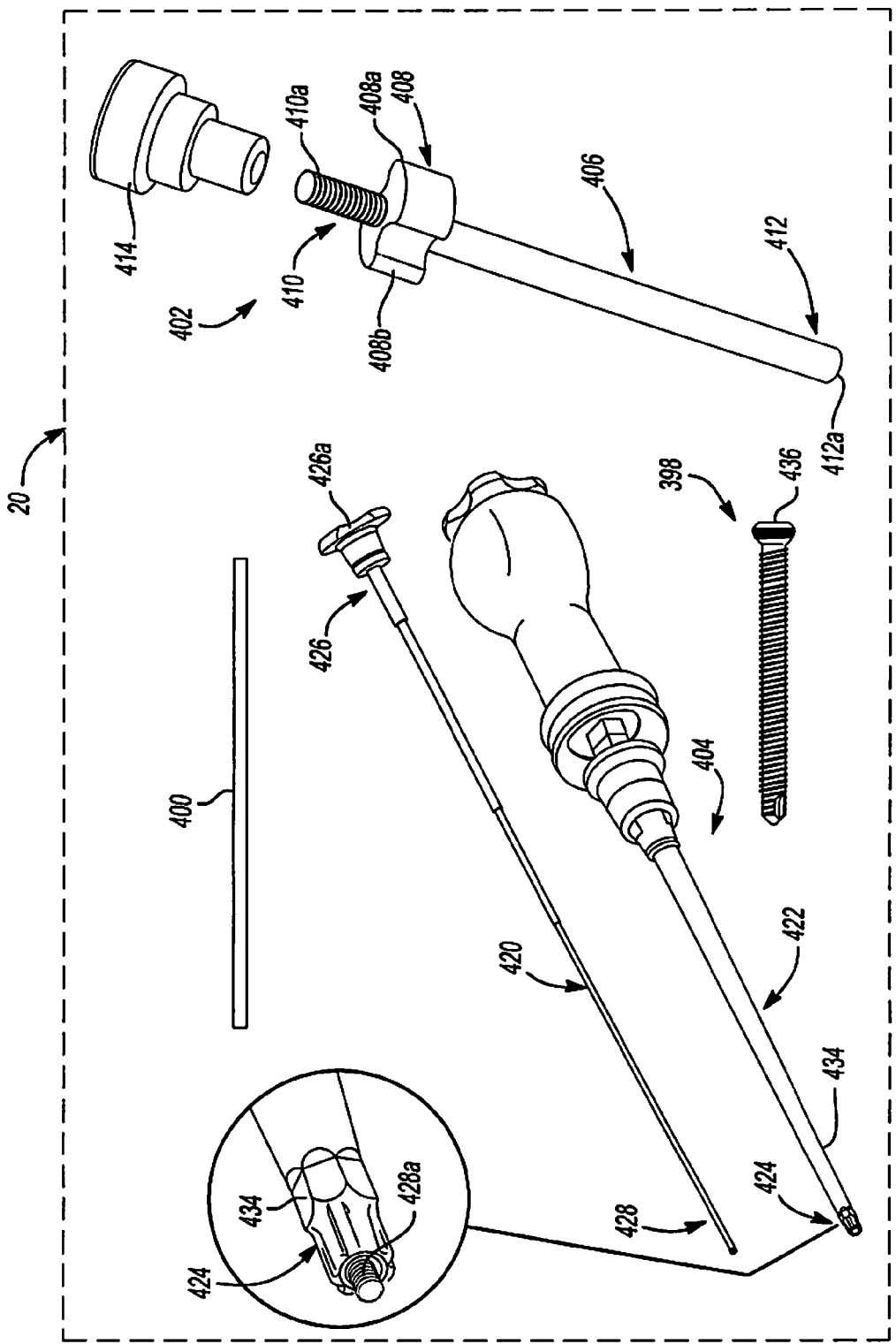
FIG. 22 is a perspective view of an exemplary anchoring system for use with the system of FIG. 1.
Figure 23:
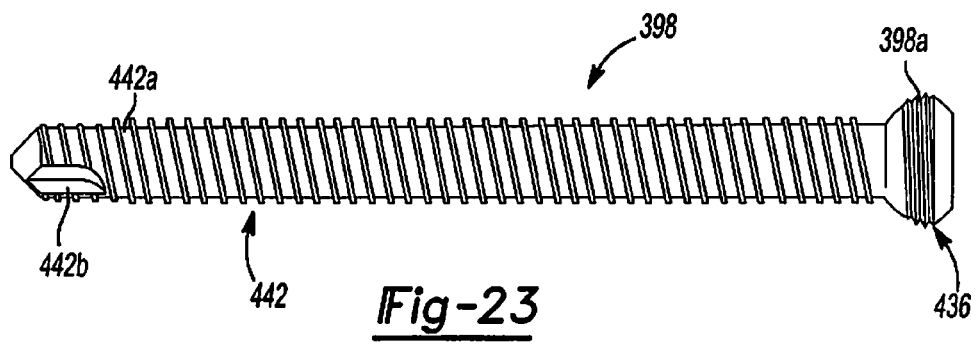
FIG. 23 is a side view of an exemplary bone fastener of the anchoring system of FIG. 22.
Figure 24:
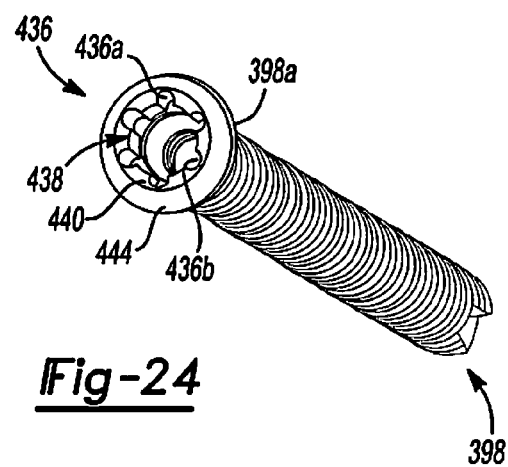
FIG. 24 is a perspective view of the bone fastener of FIG. 23.

With reference to FIGS. 1-28, a submuscular plating system 10 is shown. The submuscular plating system 10 may be particularly adapted for femoral fixation procedures. Various aspects of the present teachings, however, may have application for other procedures. In certain applications, the submuscular plating system 10 can be coupled to one or more femoral bone fragments or fractures F to secure the femoral bone fragments relative to each other in a proper alignment for healing (FIG. 1). The submuscular plating system 10 can include one or more submuscular bone plates 12 (FIGS. 2-9), a first non-targeting or first plate mounting member 14 (FIGS. 10-13), a second non-targeting or second plate mounting member 16 (FIGS. 14-16), a first targeting or third plate mounting member 18 (FIGS. 17-19), at least one targeting arm 19 (FIGS. 20 and 21) and an anchoring system 20 (FIGS. 22-24).

As will be discussed in greater detail herein, one of the first plate mounting member 14, second plate mounting member 16 and third plate mounting member 18 can be used to insert one of the submuscular bone plates 12 into the anatomy, and can also be used with the targeting arm 19 to guide the anchoring system 20 so that the anchoring system 20 can be used to couple the bone fragments F to the submuscular bone plate 12. Thus, the submuscular bone plate 12 can be used to interconnect the multiple bone fragments F to enable the bone fragments F to heal (FIG. 1). In addition, it should be noted, however, that although the submuscular plating system 10 is generally illustrated and described herein as employing a single submuscular bone plate 12 for use with a femoral fixation procedure, any number of submuscular bone plates 12 can be employed during a surgical procedure.

Further, although the submuscular plating system 10 is generally illustrated and described herein as employing one plate mounting member (14, 16, 18), any combination of plate mounting members (14, 16, 18) or subcomponents thereof can be employed during a surgical procedure. Similarly, the targeting arm 19 can be used with any of the plate mounting members (14, 16, 18) or could be used with a portion of the anchoring system 20, as will be discussed further herein.

Submuscular Bone Plates

With reference to FIGS. 2-9, the submuscular bone plates 12 can comprise a straight plate 22 (FIGS. 2-5), a first or right contoured or right flared plate 24 (FIG. 6) and a second or left contoured or left flared plate 26 (FIGS. 7-9). The bone plates 12 can be formed of a suitable biocompatible material, such as a biocompatible metal, metal alloy or polymer. In one example, the bone plates 12 can be formed from a stainless steel. Additionally, the bone plates 12 can be coated with a suitable biological coating, such as an antibiotic, bone growth agent, etc.

Each of the bone plates 12 can include a first end 28 and a second end 30. The first end 28 can include a reduced profile leading edge 28a to reduce the trauma to surrounding tissue during the insertion of the plate. The second end 30 can include at least one location feature 29a, and in one example, can include two location features 29a, 29b. The location features 29a, 29b can be keyed to a portion of the first plate mounting member 14, second plate mounting member 16 and third plate mounting member 18 to assist in coupling the portion of the first plate mounting member 14, second plate mounting member 16 and third plate mounting member 18 to the bone plate 12. In one example, the location features 29a, 29b can comprise apertures of different diameters, to ensure the proper placement of the first plate mounting member 14, second plate mounting member 16 and third plate mounting member 18 relative to the bone plate 12. It should be noted, however, that any suitable location feature could be employed to properly orientate the first plate mounting member 14, second plate mounting member 16 and third plate mounting member 18 relative to the bone plate 12.

Figure 6:
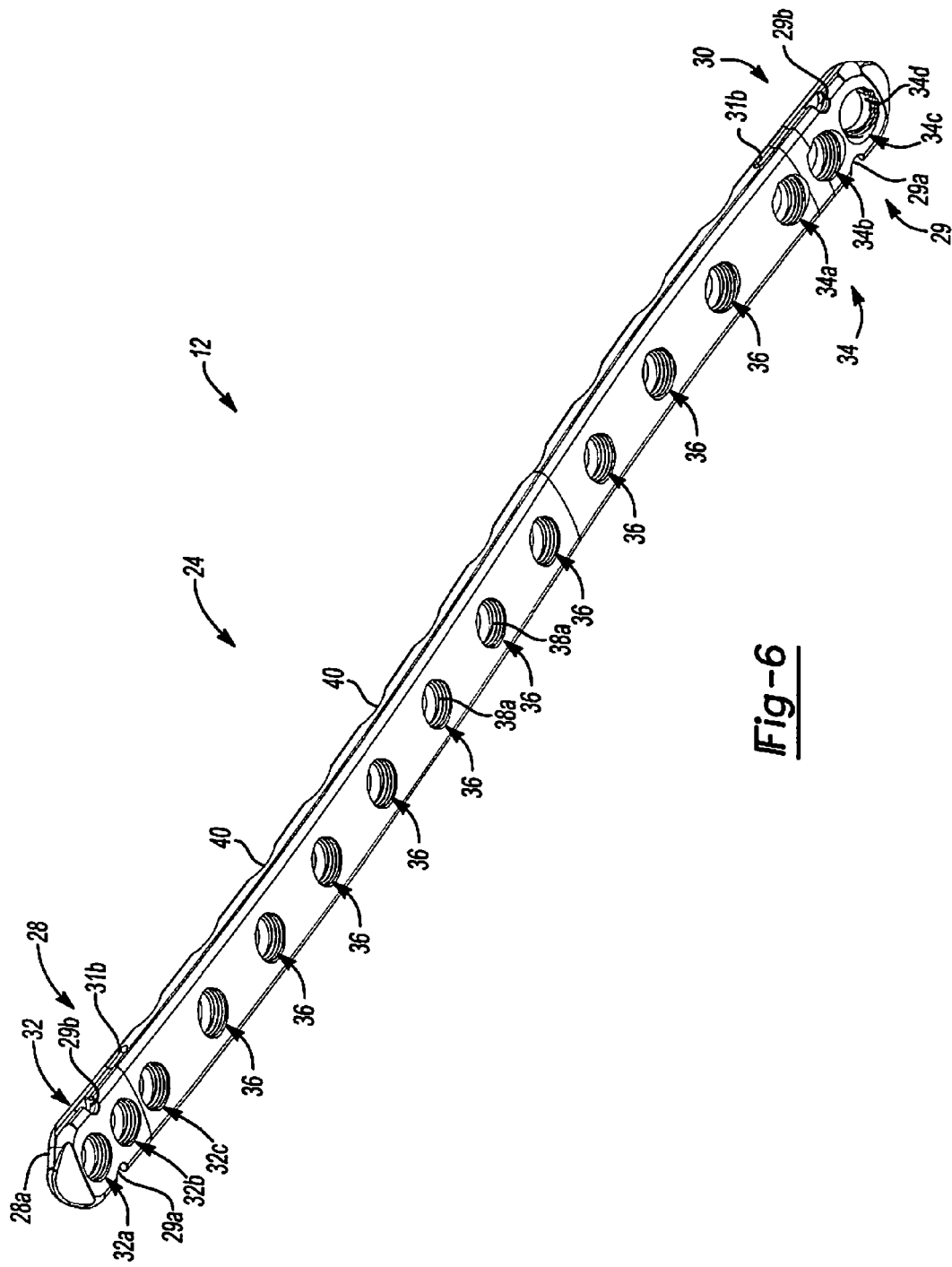
FIG. 6 is a perspective view of another exemplary bone plate for use with the system of FIG. 1.

Each of the first end 28 and the second end 30 of the bone plates 12 can also include opposing grooves 31a, 31b, as best shown in FIG. 6. The opposing grooves 31a, 31b can cooperate with the portion of the first plate mounting member 14, second plate mounting member 16 and third plate mounting member 18 to couple the first end 28 and/or second end 30 to the respective portion of the first plate mounting member 14, second plate mounting member 16 and third plate mounting member 18. It should be understood, however, that the grooves 31a, 31b could be formed to extend from the first end 28 to the second end 30 of the bone plate 12, or that only one groove 31a or 31b could be formed on the first end 28 or second end 30 of the bone plate 12, if desired. Further, while the grooves 31a, 31b are illustrated and described herein as being opposing, the grooves 31a, 31b could be offset, if desired.

The bone plates 12 can each also include a first plurality of cluster bores 32 at the first end 28 and a second plurality of cluster bores 34 at the second end 30. In one example, the first plurality of cluster bores 32 and the second plurality of cluster bores 34 can each include three closely spaced bores 32a, 32b, 32c, 34a, 34b, 34c to assist in locating the first end 28 or second end 30 of the respective bone plate 12. The first plurality of cluster bores 32a-32c and the second plurality of cluster bores 34a-34c can also be closely spaced to provide additional stability to the fracture. A distalmost bore 34c of the second plurality of cluster bores 34 can include a dual trajectory thread 34d. The dual trajectory thread 34d can be configured to receive an antegrade or retrograde bone anchor to couple the bone plate 12 to the anatomy. In addition, it should be noted that although only the distalmost bore 34c is illustrated herein as including the dual trajectory thread 34d, any or all of the bores 32a-32c, 34a, 34b, 36 could include a dual trajectory thread.

In addition, a plurality of bores 36 can be defined along each of the bone plates 12 between the first plurality of cluster bores 32 and the second plurality of cluster bores 34. In one example, the plurality of bores 36 can comprise 10 bores 36, which can be substantially equally spaced between the first plurality of cluster bores 32 and the second plurality of cluster bores 34. It should be noted, however, that although the bores 36 are illustrated herein as being formed along a line parallel to a longitudinal axis L of the bone plate 12, the bores 36 could also be staggered or offset relative to each other and/or relative to the longitudinal axis L of the bone plate 12. Additional bores can also be defined through the bone plate 12 at any desired location along the bone plate 12, if desired, such as bores for receipt of a k-wire.

Each of the plurality of bores 36, first plurality of cluster bores 32 and the second plurality of cluster bores 34 can be configured with a locking system 38, which can allow each bore 32a-32c, 34a-34c, 36 to cooperate with a bone fastener 398 of the anchoring system 20 (FIG. 22-24) to fixedly couple the bone fastener 398 to a respective bore 32a-32c, 34a-34c, 36. It should be noted, however, that the locking system 38 can be optional, and the bores 32a-32c, 34a-34c, 36 could comprise non-locking bores.

In one example, with reference to FIGS. 2-9, each bore 32a-32c, 34a-34c, 36 and each bone fastener 398 can include the SPHERELOC™ locking system commercially available from Biomet, Inc. of Warsaw, Ind., and described in commonly-owned in United States Patent Publication No. 2009/0192550, filed on Apr. 3, 2009, and incorporated by reference herein. Thus, the locking system 38 will not be described in great detail herein. Briefly, however, each bore 32a-32c, 34a-34c, 36 can have a substantially spherical shape with a plurality of threads 38a, which can threadably engage a plurality of threads 398a formed about a portion of the bone fastener 398 (FIG. 23). The engagement between the plurality of threads 38a, 398a can enable the bone fastener 398 to be releasably coupled to a respective one of the bores 32a-32c, 34a-34c, 36. It should be noted, however, that any suitable technique could be used to lock devices, such as the bone fasteners 398 to the bores 32a-32c, 34a-34c, 36, such as mating tapers, etc.

Each bone plate 12 can also include a first or front surface 37 opposite a second or back surface 39. The back surface 39 can include a plurality of scallops 40, which can be formed along outer edges 41a, 41b of the plate 22, 24, 26. The plurality of scallops 40 can be formed on opposing outer edges 41a, 41b of the bone plates 12, and can generally be formed adjacent to or between each bore 32a-32c, 34a-34c, 36 as shown best in FIGS. 5-9. The plurality of scallops 40 can reduce the mass of the bone plates 12, and can also minimize contact between the bone plate 12 and the anatomy. In addition, the plurality of scallops 40 can be visible during fluoroscopic imaging, and thus, can further aid the operator in determining the location of the bores 32a-32c, 34a-34c, 36 of the bone plate 12.

Each bone plate 12 can define a longitudinal axis L. With regard to the straight plate 22, the proximal end 28 and distal end 30 of the straight plate 22 can be parallel and co-planar with the longitudinal axis L of the straight plate 22 (FIG. 2). Regarding the right flared plate 24, as illustrated in FIGS. 6-6B, the proximal end 28 of the right flared plate 24 can be deflected, rolled or curved upwards and to the right so as to be transverse to the longitudinal axis L of the right flared plate 24. With regard to the left flared plate 26, illustrated in FIGS. 7 and 8, the proximal end 28 of the left flared plate 26 can be deflected, rolled or curved upwards and to the left so as to be transverse to the longitudinal axis L of the left flared plate 26. In one example, the proximal end 28 can be curved upwards over one or more radii of curvature.

In addition, each of the right flared plate 24 and the left flared plate 26 can have a bow radius. The bow radius can be defined between a straight portion ST associated with the proximal end 28 and a straight portion ST associated with the distal end 30 of the bone plate 12. The bow radius can have any suitable curvature that enables the right flared plate 24 and the left flared plate 26 to correspond with the geometry of the right or left femur, such as about 50 inches (in) in the case of a pediatric femur. The straight portions ST of the proximal end 28 and the distal end 30 can enable the use of the same plate mounting member (14, 16, 18) for both the right flared plate 24 and the left flared plate 26.

Each bone plate 12 can be bent into a desired angle, inserted into the anatomy and removed from the anatomy using a respective one of the first plate mounting member 14, second plate mounting member 16 and third plate mounting member 18. It should be noted that the bone plates 12 are merely exemplary, as any suitable bone plate or fixation plate could be employed with the first plate mounting member 14, second plate mounting member 16 and third plate mounting member 18, such as a straight bone plate having a contoured or flared end without a bow radius.

First Plate Mounting Member

Figure 12:
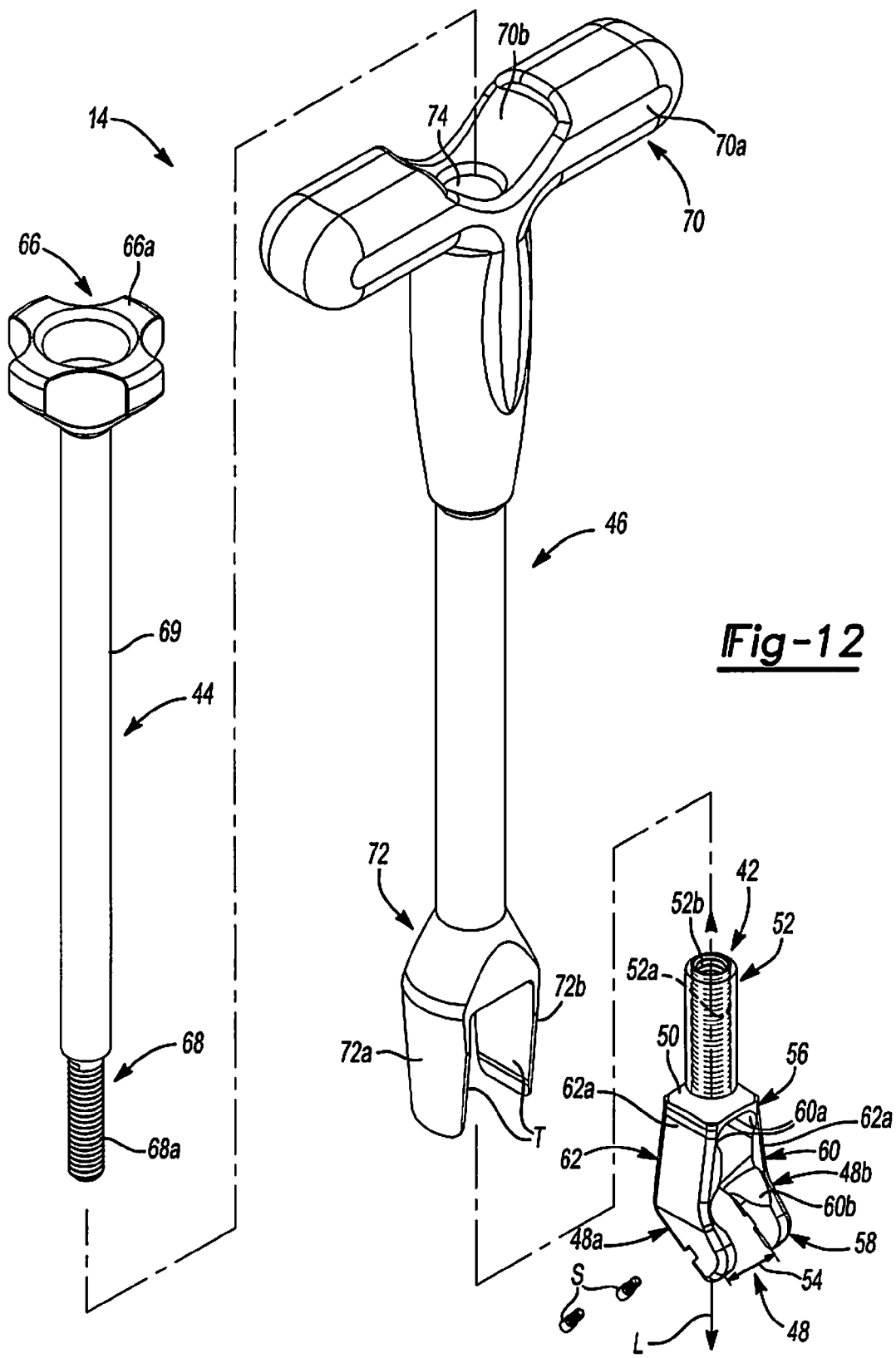
FIG. 12 is an exploded view of the plate mounting member of FIG. 10.
Figure 12A:
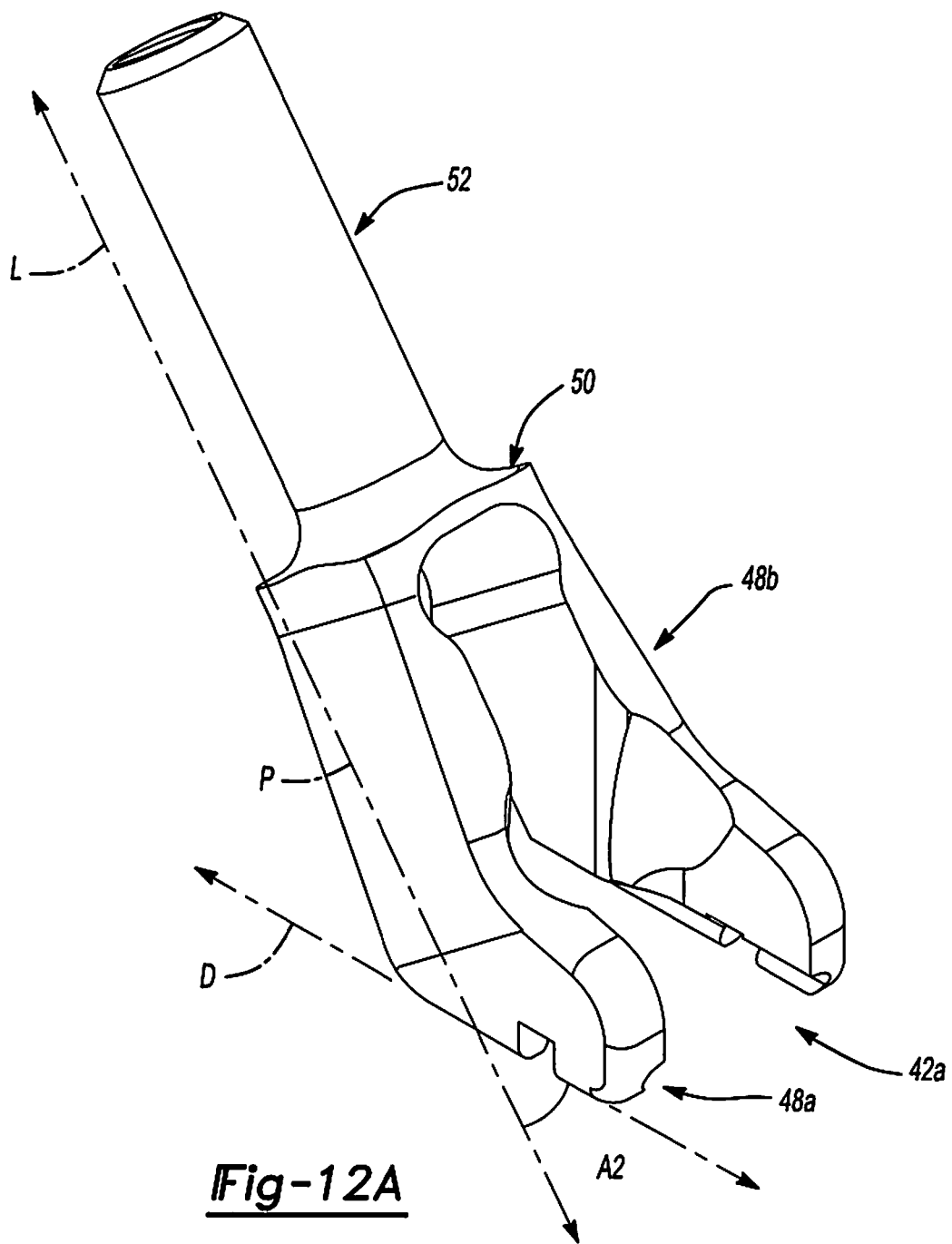
FIG. 12A is a perspective view of another exemplary forked element for use with the plate mounting member of FIG. 10.

With reference to FIGS. 10-13, the first plate mounting member 14 can include a forked member or element 42, an actuation member 44 and a housing 46. The first plate mounting member 14 can be formed of a suitable biocompatible material, such as a biocompatible metal, metal alloy or polymer. In one example, the first plate mounting member 14 can be formed from a carbon fiber. The forked element 42 can be actuated by the actuation member 44, and can cooperate with the housing 46 to couple the first plate mounting member 14 to one of the bone plates 12. The forked element 42 can be generally resilient to assist in coupling the forked element 42 to the bone plate 12. As will be discussed herein, the forked element 42 can be configured for use with a right or left flared plate 24, 26 (FIGS. 10-12, 13), while a forked element 42a can be configured for use with a straight plate 22 (FIG. 12A).

With reference to FIG. 13, each of the forked element 42 and the forked element 42a can include a pair of members or legs 48, which can extend distally from a base 50, and a coupling projection 52, which can extend proximally from the base 50. The pair of legs 48 can cooperate with the base 50 to form a fork-shape and to define a space 54. The space 54 can be generally sized to enable a respective one of the bone plates 12 to be received between the pair of legs 48, such that the pair of legs 48 can be positioned on laterally opposing sides of a respective one of the bores 32a-32c, 34a-34c, 36 of the plate 12, while still allowing access to the respective bore 32a-32c, 34a-34c, 36, as will be discussed in greater detail herein.

The pair of legs 48 can include a first leg 48a and a second leg 48. As the first leg 48a and the second leg 48b can generally be mirror images of each other about a longitudinal axis L of the forked element 42, the same reference numerals will be used with regard to the components of the first leg 48a and the second leg 48b. It should be understood that although the legs 48 are described and illustrated herein as being substantially mirror images of each other, the legs 48 need not be mirror images, and if desired, one of the legs 48 can define additional features to aid in locating the plate mounting member 14 on the bone plate 12. In the case of the legs 48 comprising mirror images of each other, the first leg 48a and the second leg 48b can each include a proximal end 56, a distal end 58, a first or interior surface 60 and a second or exterior surface 62.

The proximal end 56 of the legs 48 can be coupled to the base 50. As best shown in FIGS. 12A and 13, the proximal end 56 can extend along an axis P, which can be parallel to the longitudinal axis L of the forked element 42, 42a. The distal end 58 can include a bottom surface 64 and a rounded tip 66. The bottom surface 64 can include a threaded bore 64a and a lip 64b. The threaded bore 64a can receive a pin or screw S. The screw S can cooperate with the location features 29a, 29b to position the legs 48 on the respective plate 12 as will be discussed in greater detail herein. It will be understood, however, that the screws S are merely exemplary, as any desired feature could be used to locate the legs 48 on the bone plate 12, such as a dovetail pins, etc.

The lip 64b can assist in locating the forked element 42, 42a onto the bone plate 12. The lip 64b can extend distally from the bottom surface 64 and can be configured to engage a respective outer edge 41a, 41b of the respective bone plate 12 when the forked element 42, 42a is coupled to the bone plate 12, as best shown in FIG. 11. In addition, the lip 64b can define a mating projection M, which can be sized to engage a respective one of the grooves 31a, 31b, when the forked element 42, 42a is coupled to the bone plate 12. It should be noted, however, that the lip 64b and screw S can be integrated into one feature to enable the forked element 42, 42a to be located onto the bone plate 12 and also grip the bone plate 12 substantially simultaneously, such as one or more dovetail pins. In addition, the lip 64b could also be configured so as to grip onto the back surface 39 of the bone plate 12, if desired.

With reference to FIG. 13, the bottom surface 64 can generally extend along an axis D, which can be transverse to the longitudinal axis L of the forked element 42, 42a, but parallel to a longitudinal axis L of the bone plates 12. Thus, the proximal end 56 of the forked element 42, 42a, can be angled relative to the bottom surface 64 of the distal end 58 and to the bone plates 12.

In the example of a forked element 42, with reference to FIG. 13, the proximal end 56 can be angled relative to the bottom surface 64 and the bone plates 12 by about 15 degrees to about 50 degrees. It should be noted, however, the proximal end 56 could be angled at any desired degree relative to the bone plate 12, or could not be angled relative to the bottom surface 64 and the bone plate 12 (i.e. an in-line configuration), if desired. In the example of a forked element 42a, with reference to FIG. 12A, the proximal end 56 can be angled relative to the bottom surface 64 of the bone plates 12 by an angle A2 less than an angle A1 associated with the forked element 42. In this regard, the forked element 42, 42a can be used to compensate for the difference between the straight plate 22 and the left or right flared plate 24, 26 such that the distance between the bone plate 12 and the targeting arm 19 remains constant or fixed regardless of the bone plate 12 utilized.

As will be discussed in greater detail herein, by forming the forked element 42, 42a such that the proximal end 56 is offset or angled relative to the distal end 58, each and every bore 32a-32c, 34a-34c, 36 in the bone plate 12 can be accessible by the operator, even when the first plate mounting member 14 is coupled to a respective bone plate 12. The rounded tip 66 of the distal end 58 can facilitate the advancement of the distal end 58 through soft tissue during the insertion of the bone plate 12 into the anatomy.

The interior surface 60 of the forked element 42, 42a can extend from the proximal end 56 to the distal end 58. The interior surface 60 can include a first contoured recess 60a and a second contoured recess 60b, as best shown in FIGS. 10-12. The first contoured recess 60a of the first leg 48a and the first contoured recess 60a of the second leg 48b can cooperate to define an aperture, which can be sized to allow a portion of the anchoring system 20 to be inserted through the legs 48 and into a respective bore 32a-32c, 34a-34c, 36 of the bone plate 12. Similarly, the second contoured recess 60b of the first leg 48a and the second contoured recess 60b of the second leg 48b can cooperate to define an aperture, which can be sized to allow a portion of the anchoring system 20 to be inserted through the legs 48 and into a respective bore 32a-32c, 34a-34c, 36 of the bone plate 12.

With reference to FIG. 12, the exterior surface 62 can define a taper 62a. The taper 62a can cooperate with the housing 46 to couple the forked element 42, 42a to the bone plate 12, when actuated by the actuation member 44, as will be discussed in greater detail herein.

The base 50 can cooperate with the housing 46 to define a stop for the actuation of the actuation member 44, as illustrated in FIG. 13. In this regard, as will be discussed, the base 50 can contact a portion of the housing 46 to prevent further retraction of the forked element 42, 42a within the housing 46, which thereby limits further actuation of the actuation member 44.

With reference to FIGS. 12 and 13, the coupling projection 52 can extend proximally from the base 50, and can define a bore 52a having a plurality of threads 52b. The bore 52a can threadably receive a portion of the actuation member 44 such that rotation of the actuation member 44 can move the forked element 42, 42a linearly with respect to the housing 46. In other words, the rotation of the actuation member 44 can cause the forked element 42, 42a to translate relative to the housing 46, which can couple or uncouple the forked element 42, 42a from the bone plate 12, as will be discussed. It should be noted, however, that any suitable technique could be employed to move the forked element 42, 42a relative to the housing 46, and further, that the plurality of threads 52b could be defined about the coupling projection 52 and the coupling projection 52 could be threadably received within a bore defined by the actuation member 44.

With reference to FIGS. 10-13, the actuation member 44 can be coupled to the coupling projection 52 of the forked element 42, 42a and can be manipulated by an operator to move the forked element 42, 42a relative to the housing 46. The actuation member 44 can be composed of any suitable biocompatible material, such as a biocompatible metal, metal alloy, polymer or combination thereof. With reference to FIGS. 12 and 13, the actuation member 44 can include a proximal end 66 coupled to a distal end 68 via an elongate body 69. The proximal end 66 can include a first graspable portion or knob 66a, which can be manipulated or rotated by an operator to move the forked element 42, 42a relative to the housing 46. The distal end 68 can include a plurality of threads 68a, which can threadably engage the plurality of threads 52b formed in the coupling projection 52 to couple the actuation member 44 to the forked element 42, 42a. Although described and illustrated herein as a discrete component, the actuation member 44 could be integrated into the housing 46, if desired.

With reference back to FIGS. 10-13, the housing 46 can include a proximal end 70, a distal end 72 and a central bore 74 (FIG. 13), which can extend from the proximal end 70 to the distal end 72. The central bore 74 can be sized to rotatably receive the actuation member 44 therethrough, and can also be sized to prevent the base 50 of the forked element 42, 42a from advancing into the central bore 74. The proximal end 70 can include a second graspable portion or handle 70a having a recessed surface 70b. The recessed surface 70b can allow the knob 66a to rotate relative to the handle 70a.

The distal end 72 can include a pair of laterally opposed members 72a, 72b, which can be spaced apart to receive the forked element 42, 42a therebetween. The laterally opposed members 72a, 72b can be generally symmetrical about a longitudinal axis of the housing 46, however, the laterally opposed members 72a, 72b could be offset relative to the longitudinal axis, if desired. The laterally opposed members 72a, 72b can include a mating tapered surface T, which can cooperate with the taper 62a on the exterior surface 62 of the forked element 42, 42a to couple the respective bone plate 12 to the first plate mounting member 18. In addition, if desired, an extension 73 can be formed between the laterally opposed members 72a, 72b to couple the laterally opposed members 72a, 72b to each other. The extension 73 can impart additional rigidity to the housing 46.

In this regard, in order to assemble the first plate mounting member 14, the actuation member 44 can be inserted through the central bore 74 of housing 46. Then, the distal end 68 of the actuation member 44 can be threadably engaged with the plurality of threads 52b of the coupling projection 52 of the forked element 42, 42a. Generally, the distal end 68 of the actuation member 44 can be at least partially engaged with the plurality of threads 52b such that further rotation of the knob 66a of the actuation member 44 can operate to draw the forked element 42, 42a into contact with the laterally opposed members 72a, 72b of the housing 46. In a first position, the actuation member 44 can be engaged with the forked element 42, 42a such that the taper 62a of the exterior surface 62 of the forked element 42, 42a is not in substantial contact with the mating taper T of the laterally opposed members 72a, 72b. In this first position, the bottom surface 64 of the legs 48 can be positioned onto the bone plate 12 such that the screws S can be received within the location features 30a, 30b of the bone plate 12 and the lip 64b can be positioned about the outer edges 41a, 41b of the bone plate 12.

From the first position, the knob 66a can be rotated by the operator, which can move the forked element 42, 42a from the first position to a second position. In the second position, the forked element 42, 42a can be retracted into the housing 46 or translated rearward such that the taper 62a of the exterior surface 62 of the forked element 42, 42a is in contact with the mating taper T of the laterally opposed members 72a, 72b. The contact between the taper 62a and the mating taper T can cause the legs 48 to compress, which in turn can couple or clamp the bone plate 12 to the forked element 42, 42a. It should be noted that while the first plate mounting member 14 is coupled to the bone plate 12, each of the bores 32a-32c, 34a-34c, 36 of the bone plate 12 are accessible by the operator.

With the bone plate 12 coupled to the forked element 42, 42a, the first plate mounting member 14 can be used to insert the bone plate 12 into the anatomy. The first plate mounting member 14 can also be used to bend the bone plate 12 into a desired shape prior to insertion. The first plate mounting member 14 can also be used to remove the bone plate 12 from the anatomy, if desired. Further detail regarding the insertion and removal of a respective plate 12 will be discussed in greater detail herein.

Second Plate Mounting Member

Figure 15:
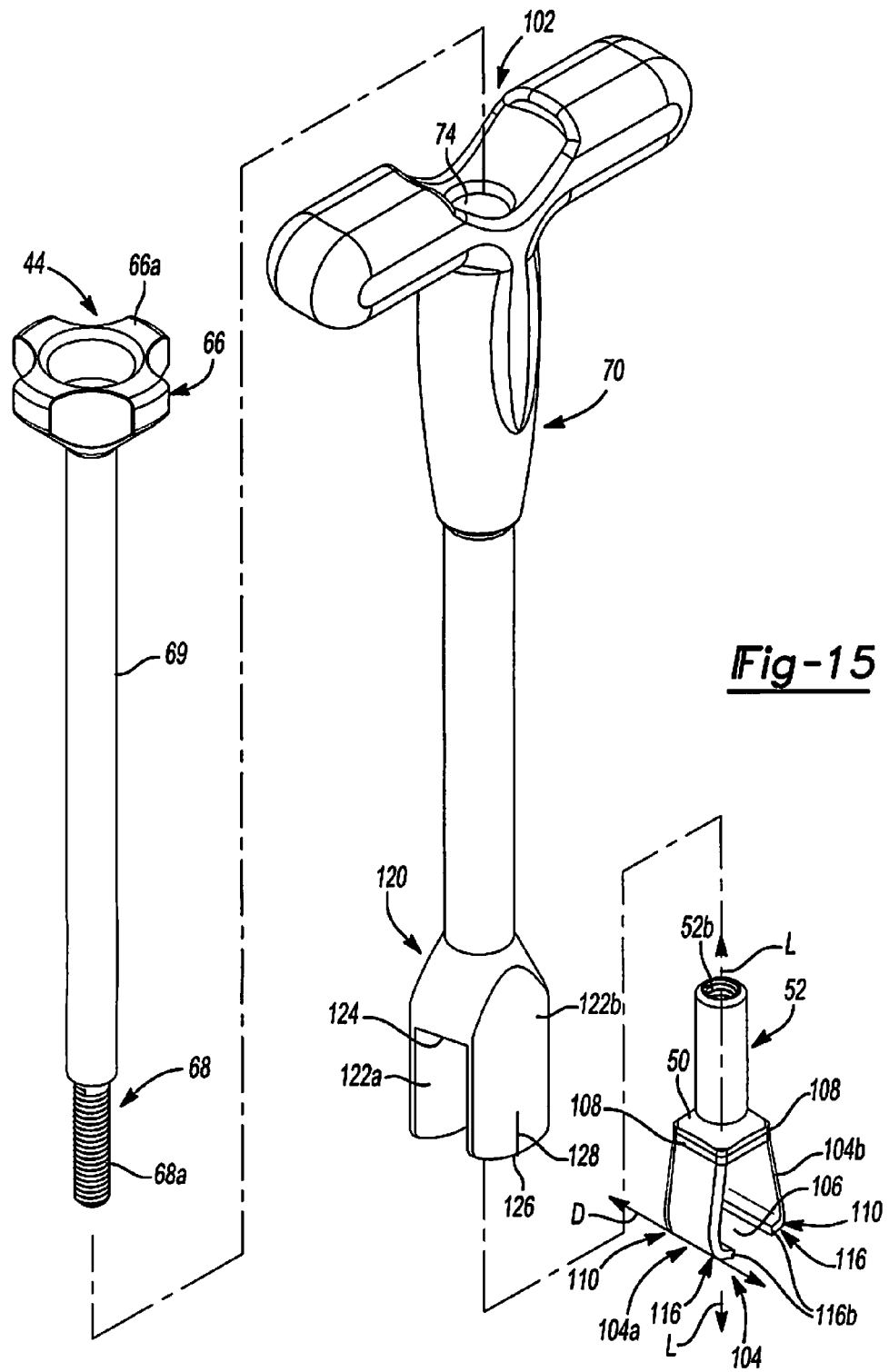
FIG. 15 is an exploded view of the plate mounting member of FIG. 14.

With reference now to FIGS. 14-16, in one example, the second plate mounting member 16 can be employed to repair a damaged portion of an anatomy. As the second plate mounting member 16 can be similar to the first plate mounting member 14 described with reference to FIGS. 10-13, only the differences between the first plate mounting member 14 and the second plate mounting member 16 will be discussed in great detail herein, and the same reference numerals will be used to denote the same or similar components. The second plate mounting member 16 can be formed of a suitable biocompatible material, such as a biocompatible metal, metal alloy or polymer. In one example, the second plate mounting member 16 can be formed from a carbon fiber.

With continued reference to FIGS. 14-16, the second plate mounting member 16 can include a forked member or element 100, an actuation member 101 and a housing 102. The forked element 100 can be actuated by the actuation member 101, and can cooperate with the housing 102 to couple the second plate mounting member 16 to the bone plate 12. With reference to FIGS. 15 and 16, the forked element 100 can include a pair of members or legs 104, which can extend distally from the base 50, and a coupling projection 105, which can extend proximally from the base 50. The pair of legs 104 can cooperate with the base 50 to form a fork-shape and to define a space 106. The space 106 can be generally sized to enable a respective one of the submuscular bone plates 12 to be received between the pair of legs 104, such that the pair of legs 104 can be positioned on laterally opposing sides of a respective one of the bores 32a-32c, 34a-34c, 36 of the bone plate 12, as will be discussed in greater detail herein.

The pair of legs 104 can include a first leg 104a and a second leg 104b. As the first leg 104a and the second leg 104b can generally be mirror images of each other about a longitudinal axis L of the forked element 100, the same reference numerals will be used with regard to the components of the first leg 104a and the second leg 104b. The first leg 104a and the second leg 104b can each include a proximal end 108, a distal end 110, a first or interior surface 112 and a second or exterior surface 114.

The proximal end 108 of the legs 104 can be coupled to the base 50. The distal end 110 can include a bottom surface 116. The bottom surface 116 can include a lip 116b. The lip 116b can extend inward from the bottom surface 116 and can be configured to engage the back surface 39 of a respective bone plate 12 when the forked element 100 is coupled to the bone plate 12. In other words, the lip 116b can project into the space 106 defined by the legs 104 to capture the bone plate 12 within the space 106. The lip 116b can include surface features to facilitate coupling the bone plate 12 to the forked element 100, such as teeth, ribs, ridges, a roughened surface, etc. It should be noted that although the lip 116b is illustrated and described herein as cooperating with the back surface 39 of the bone plate 12, the lip 116b could cooperate with the grooves 31a, 31b, if desired.

Generally, with reference to FIG. 16, the bottom surface 116 can extend along an axis D, which can be transverse to the longitudinal axis L of the housing 102 of the second plate mounting member 16, but parallel to a longitudinal axis L of the bone plates 12. Thus, the forked element 100 can enable the housing 102 to be angled relative to the bone plate 12. In one example, the housing 102 can be angled relative to the bone plate 12 by about 15 degrees to about 50 degrees, however, the housing 102 could be angled at any desired degree relative to the bone plate 12, or could be in-line with the bone plate 12, if desired.

The interior surface 112 can extend from the proximal end 108 to the distal end 110. The interior surface 112 can be sized to contact the outer edges 41a, 41b of the respective bone plate 12 when the bone plate 12 is coupled to the second plate mounting member 16. The exterior surface 114 can define a taper 114a. The taper 114a can cooperate with the housing 102 to couple the forked element 100 to one of the bone plate 12, when actuated by the actuation member 101, as will be discussed in greater detail herein. It should be noted that the use of a taper 114a is merely exemplary, as any mating interface could be employed to couple the forked element 100 to the bone plate 12.

With reference to FIGS. 15 and 16, the coupling projection 105 can extend proximally from the base 50, and can define a plurality of threads 105a. The plurality of threads 105a can be threaded into a portion of the actuation member 101 such that rotation of the actuation member 101 can move the forked element 100 linearly with respect to the housing 102. In other words, the rotation of the actuation member 101 can cause the forked element 100 to translate relative to the housing 102, as will be discussed. It should be noted, however, that any suitable technique could be employed to move the forked element 100 relative to the housing 102, and further, that the plurality of threads 105a could be defined about the actuation member 101 and the coupling projection 52 define a threaded bore, if desired.

The actuation member 101 can be coupled to the coupling projection 105 of the forked element 100 and can be manipulated by an operator to move the forked element 100 relative to the housing 102. The actuation member 101 can be composed of any suitable biocompatible material, such as a biocompatible metal, metal alloy, polymer or combination thereof. The actuation member 101 can include the proximal end 66 coupled to a distal end 119 via an elongate body 69. The elongate body 69 can be cannulated to enable a guidewire to pass through the actuation member 101, from the proximal end 66 to the distal end 119, if desired. The distal end 119 of the actuation member 101 can include a threaded bore 119a, which can threadably receive the plurality of threads 105a formed about the coupling projection 105 to couple the actuation member 101 to the forked element 100. Although described and illustrated herein as a discrete component, the actuation member 101 could be integrated into the housing 102, if desired.

Figure 15A:
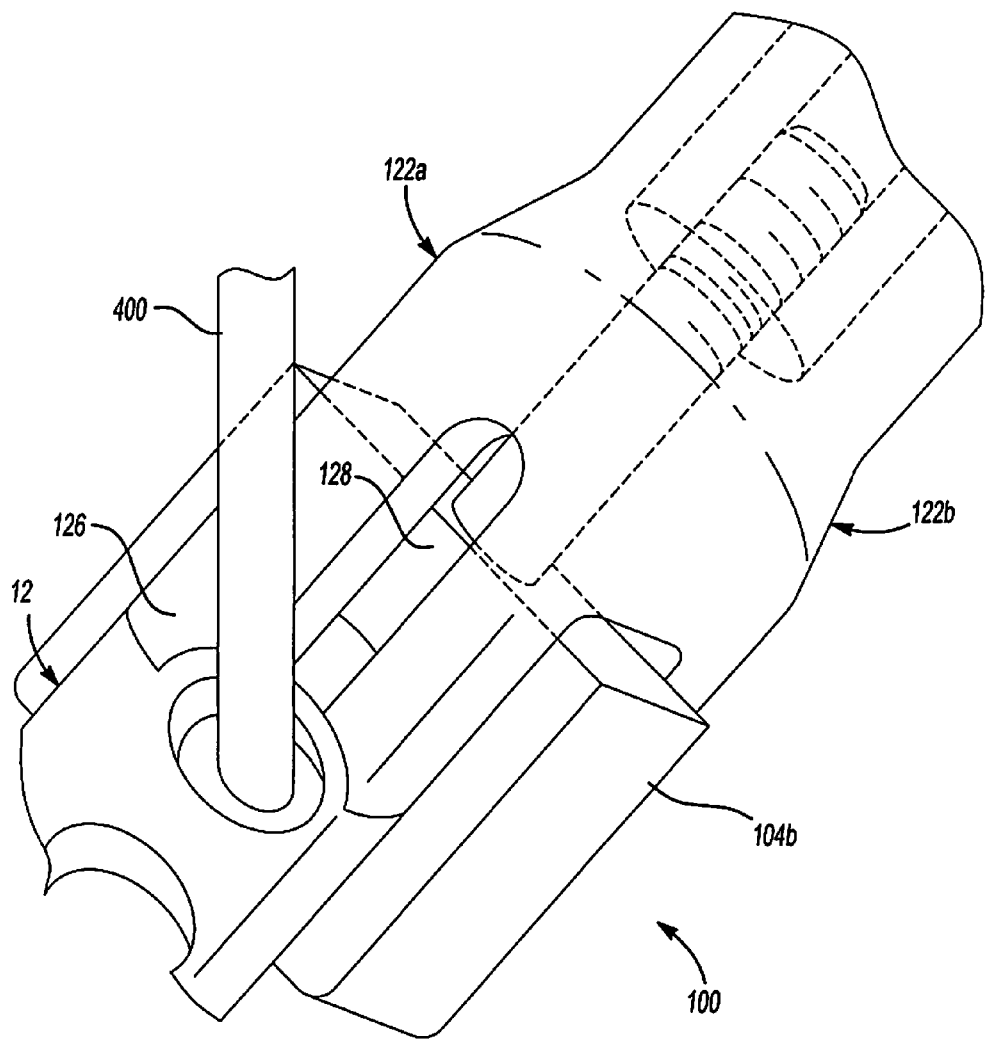
FIG. 15A is a detailed illustration of a portion of an exemplary housing for the plate mounting member of FIG. 14.

With reference to FIGS. 14-16, the housing 102 can include the proximal end 70, a distal end 120 and the central bore 74. The distal end 120 can include a pair of laterally opposed members 122a, 122b, which can be spaced apart by a channel 124. The laterally opposed members 122a, 122b can be generally symmetrical about a longitudinal axis of the housing 102. The laterally opposed members 122a, 122b can include a scallop 126 and a slot 128, as best illustrated in FIG. 15A. The scallop 126 can provide additional surface area for contacting the bone plate 12 when the second plate mounting member 16 is coupled to the bone plate 12. The slot 128 can enable the laterally opposed members 122a, 122b to flex or bend, which can allow the bone plate 12 to be securely coupled to the second plate mounting member 16.

With reference to FIGS. 14-16, the channel 124 of the distal end 120 can receive the forked element 100. The forked element 100 can be movable relative to the channel 124 to couple or uncouple the bone plate 12 from the second plate mounting member 16. A portion of the channel 124 can contact the exterior surface 114 of the forked element 100 to couple the respective bone plate 12 to the second plate mounting member 16.

In this regard, in order to assemble the second plate mounting member 16, the actuation member 101 can be inserted through the central bore 74 of housing 102. Then, the distal end 119 of the actuation member 101 can be threadably engaged with the plurality of threads 105a of the coupling projection 105 of the forked element 100. Generally, the distal end 119 of the actuation member 101 can be at least partially engaged with the plurality of threads 105a such that further rotation of the knob 56a of the actuation member 101 can operate to draw the forked element 100 into contact with the channel 124 of the housing 102 (FIG. 15). In a first position, the actuation member 101 can be engaged with the forked element 100 such that the lips 116a of the forked element 100 can be positioned about the back surface 39 of the bone plate 12.

Then, the knob 56a of the actuation member 101 can be rotated by the operator, which can move the forked element 100 from the first position to a second position. In the second position, the forked element 100 can be retracted into the housing 102 or translated rearward such that the exterior surface 114 of the forked element 100 is in contact with the channel 124. The contact between the channel 124 and the forked element 100 can couple or clamp the bone plate 12 to the forked element 100.

With the bone plate 12 coupled to the forked element 100, the second plate mounting member 16 can be used to insert the bone plate 12 into the anatomy. The second plate mounting member 16 can also be used to bend the bone plate 12 into a desired shape prior to insertion. The second plate mounting member 16 can also be used to remove the bone plate 12 from the anatomy, if desired. During the removal of the bone plate 12 from the anatomy using the second plate mounting member 16, the distal end 110 of the forked element 100 can act as a chisel to remove boney in-growth formed along the bone plate 12. Further detail regarding the insertion and removal of a respective bone plate 12 will be discussed in greater detail herein.

Third Plate Mounting Member

Figure 17:
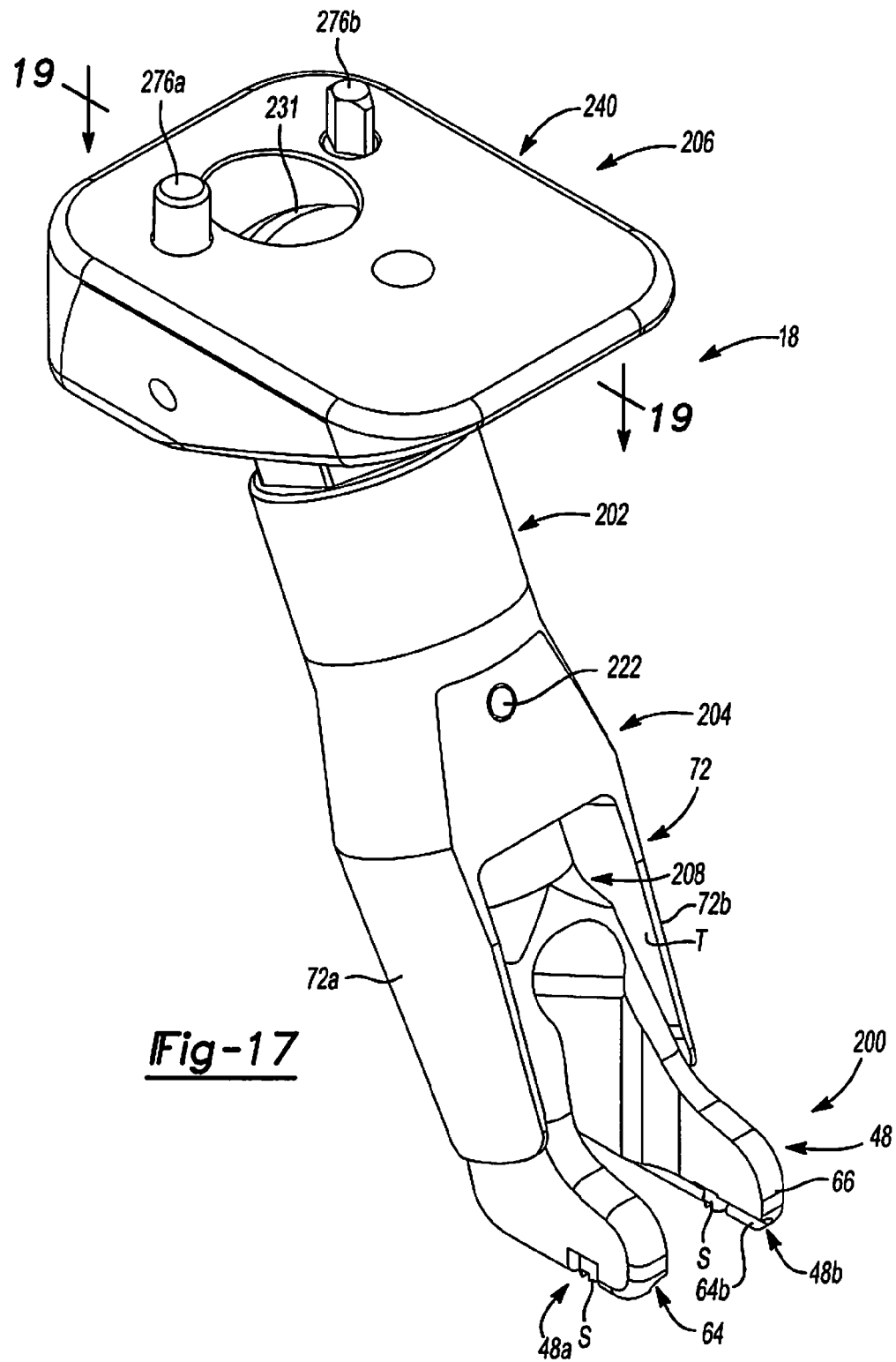
FIG. 17 is a perspective view of another exemplary plate mounting member for use with the system of FIG. 1.
Figure 18:
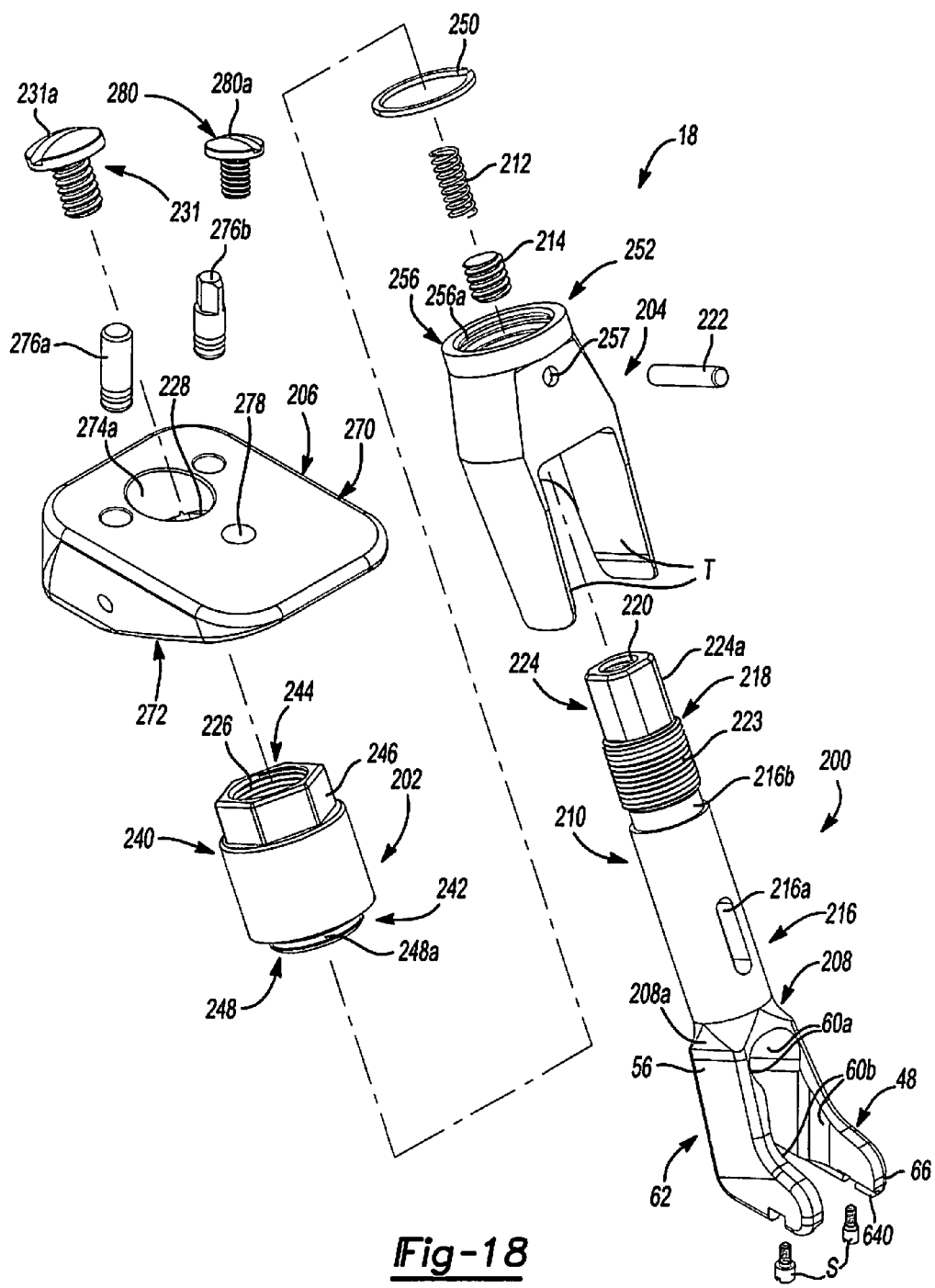
FIG. 18 is an exploded view of the plate mounting member of FIG. 17.
Figure 19:
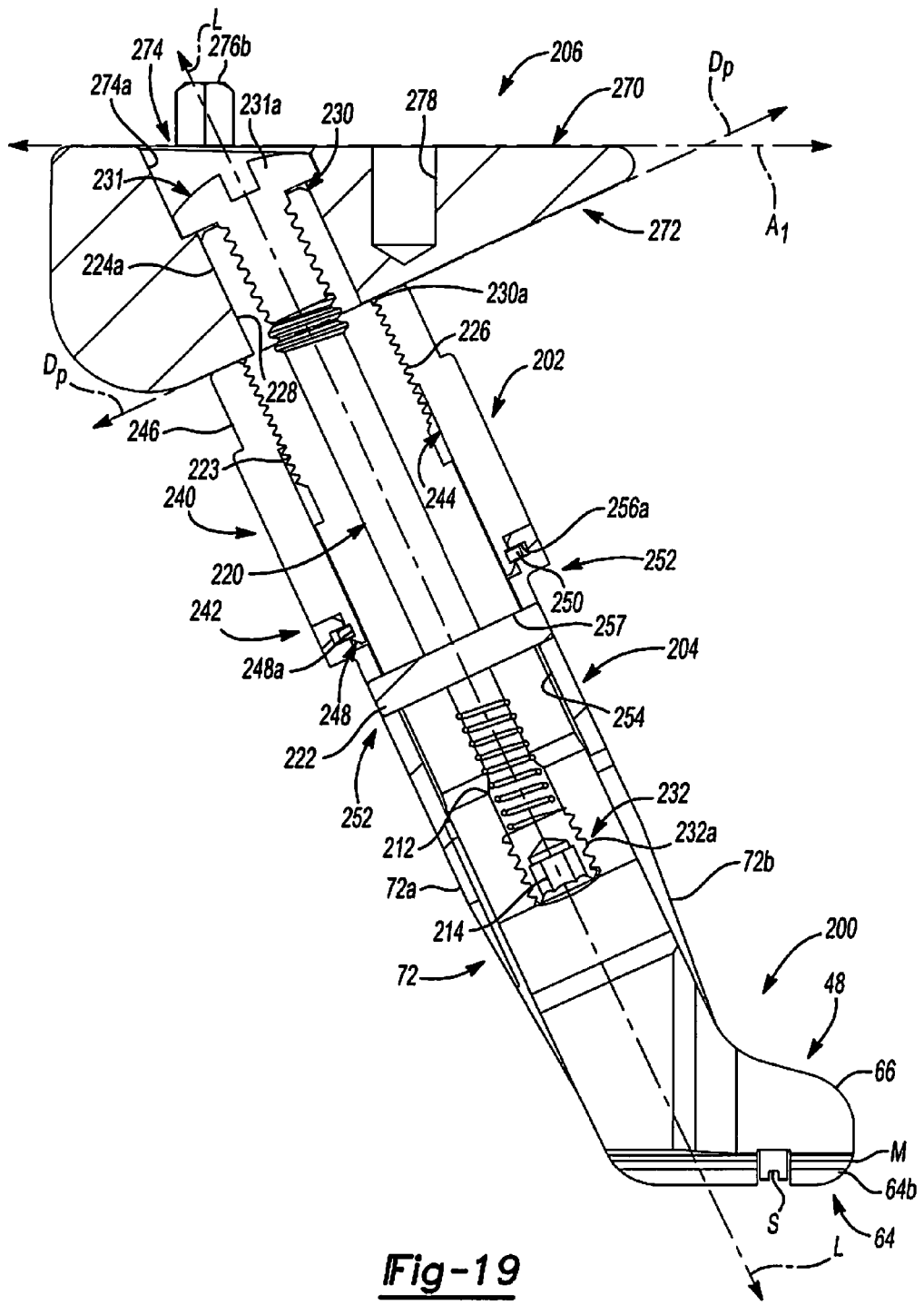
FIG. 19 is a cross-sectional view of the plate mounting member of FIG. 17, taken along line 19-19 of FIG. 17.

With reference now to FIGS. 17-19, in one example, the third plate mounting member 18 can be employed to repair a damaged portion of an anatomy. As the third plate mounting member 18 can be similar to the first plate mounting member 14 described with reference to FIGS. 10-13, only the differences between the first plate mounting member 14 and the third plate mounting member 18 will be discussed in great detail herein, and the same reference numerals will be used to denote the same or similar components. The third plate mounting member 18 can be formed of a suitable biocompatible material, such as a biocompatible metal, metal alloy or polymer. In one example, the third plate mounting member 18 can be formed from a carbon fiber.

With reference to FIGS. 17-19, the third plate mounting member 18 can include a forked member or element 200, an actuation member 202, a housing 204 and a platform 206. The forked element 200 can be actuated by the actuation member 202, and can cooperate with the housing 204 to couple the third plate mounting member 18 to one of the bone plates 12. The platform 206 can support the targeting arm 19 relative to the bone plate 12, as will be discussed herein.

With reference to FIGS. 18 and 19, the forked element 200 can include the pair of members or legs 48, which can extend distally from a base 208, and a coupling projection 210, which can extend proximally from the base 208. The forked element 200 can also include a spring 212, which can be retained within the forked element 200 by a set screw 214, as will be discussed.

Figure 17A:
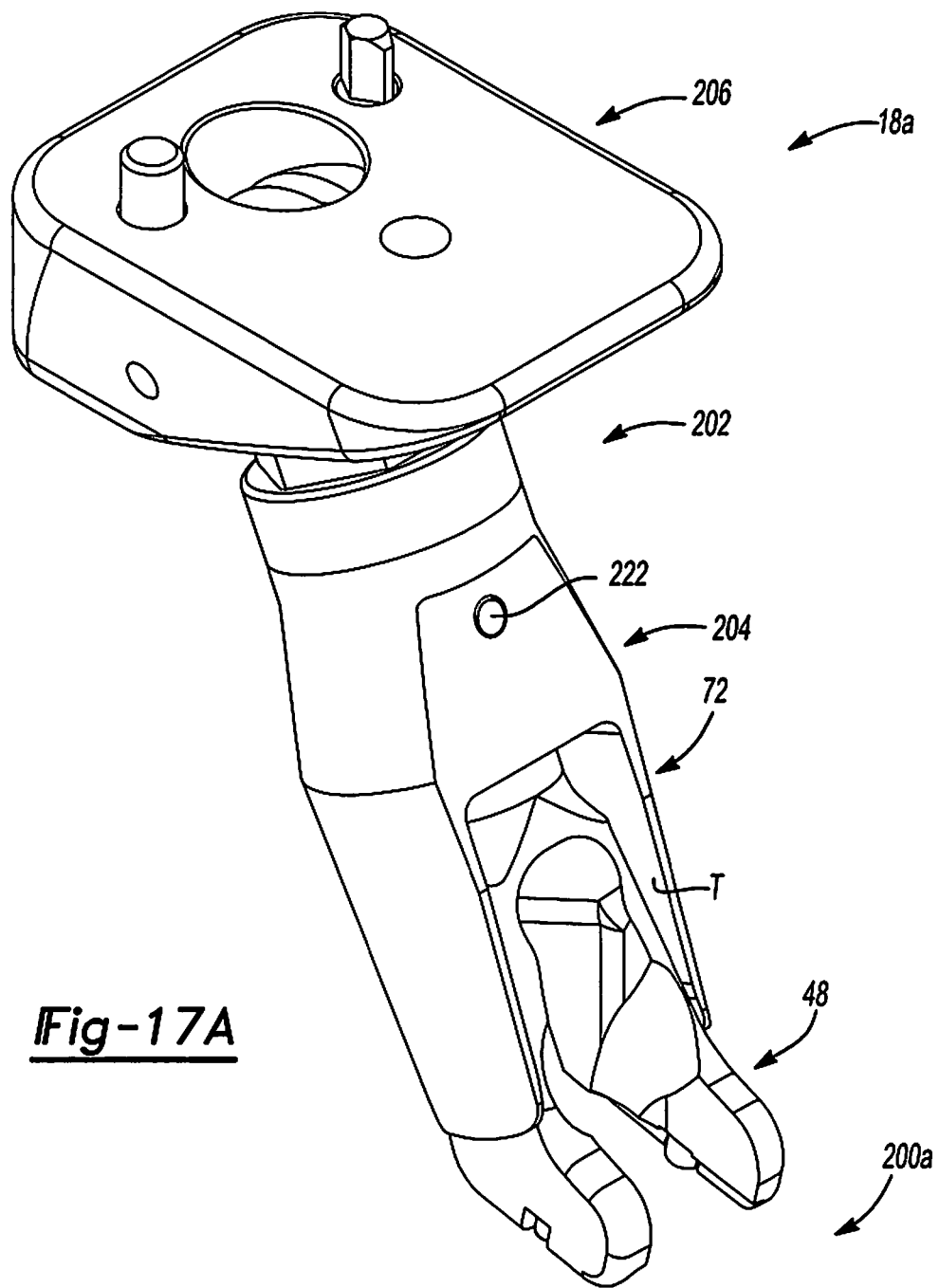
FIG. 17A is a perspective view of another exemplary forked element for use with the plate mounting member of FIG. 17.

The pair of legs 48 can cooperate with the base 208 to form a fork-shape and to define the space 54. The space 54 can be generally sized to enable a respective one of the submuscular bone plates 12 to be received between the pair of legs 48, such that the pair of legs 48 can be positioned on laterally opposing sides of a respective one of the bores 32a-32c, 34a-34c, 36 of the bone plate 12, while still allowing unobstructed access to the respective bore 32a-32c, 34a-34c, 36, as will be discussed in greater detail herein. The bottom surface 64 of the legs 48 of the forked element 200 can also be angled with an angle A1 relative to the longitudinal axis L for use with the left or right flared plate 24, 26 (FIGS. 17, 18, 19) or can be angled with an angle of A2 relative to the longitudinal axis for use with the straight plate 22. An exemplary third plate mounting member 18a employing a forked element 200a with legs 48 for use with the straight plate 22 is illustrated in FIG. 17A.

The base 208 can cooperate with the housing 204 to move the legs 48 between a first position, in which the legs 48 can be positioned about or uncoupled from the bone plate 12, and a second position, in which the legs 48 can be coupled or clamped to the bone plate 12. It should be noted that the use of the legs 48 is merely exemplary, as any suitable technique could be used to couple and uncouple the bone plate 12 from the third plate mounting member 18, such as the use of a clamping jaw, hinges, etc. The base 208 can include a taper 208a, which can be formed on opposing sides of the base 208 so as to be adjacent to the proximal end 56 of each of the legs 48a, 48b. The taper 208a can be configured to mate with a mating taper T formed on a portion of the housing 204 to move or drive the legs 48 between the first position and the second position, as will be discussed herein.

The coupling projection 210 can extend proximally from the base 208. The coupling projection 210 can include a first end 216, a second end 218 and a central bore 220. The first end 216 can be coupled to the base 208, and can be substantially cylindrical in shape. The first end 216 can include an elongate slot 216a, which can intersect and pass through at least a portion of the central bore 220. It should be noted that the slot 216a can be optional, and if employed, can further control or constrain the movement of the housing 204 relative to the forked element 200. In this regard, the slot 216a can be configured to receive a pin 222, which can be coupled to the housing 204. The engagement of the pin 222 within the slot 216a can control or constrain the movement of the housing 204 to translational or linear movement relative to the forked element 200. The first end 216 can be spaced apart from the second end 218 by a reduced diameter portion 216b. The reduced diameter portion 216b can act as a stop for the further advancement or movement of the actuation member 202 relative to the forked element 200, as will be discussed in greater detail herein.

The second end 218 can include a plurality of threads 223 and a platform mounting feature 224. The plurality of threads 223 can be adjacent to the reduced diameter portion 216b, and in one example, can be defined between the reduced diameter portion 216b and the platform mounting feature 224. The plurality of threads 223 can matingly engage a plurality of threads 226 formed on the actuation member 202 to enable the actuation member 202 to rotate about the forked element 200. As will be discussed, the rotation of the actuation member 202 about the forked element 200 can cause the housing 204 to move between the first, uncoupled position and the second, coupled position.

The platform mounting feature 224 can provide a keyed feature for coupling or mounting the platform 206 relative to the forked element 200. Generally, the platform mounting feature 224 can cooperate with the platform 206 to prevent the movement (rotational or translational) of the platform 206 relative to the forked element 200. In one example, the platform mounting feature 224 can comprise a square stem 224a, however, the platform mounting feature 224 could comprise any suitable mechanism that prevents the movement of the platform 206 relative to the forked element 200, such as a hexagonal stem, octagonal stem, pentagonal stem, etc. The square stem 224a can mate with a square bore 228 defined in the platform 206 to assist in non-movably coupling the platform 206 to the forked element 200. By non-movably coupling the platform 206 to the forked element 200, the distance between the platform 206 and the forked element 200 can remain constant or fixed throughout the surgical procedure and the platform 206. This can provide additional accuracy in coupling the anchoring system 20 to the bone plate 12, as will be discussed herein.

With reference to FIG. 19, the central bore 220 can be defined through the coupling projection 210. The central bore 220 can have a first end 230 and a second end 232. The first end 230 can include a plurality of threads 230a, which can threadably receive a mechanical fastener 231, to couple the platform 206 to the forked element 200, as will be discussed herein. The second end 232 can also include a plurality of threads 232a, which can threadably receive the set screw 214. The set screw 214 can retain the spring 212 within the central bore 220.

In this regard, the spring 212 can be received within the second end 232 of the central bore 220 and retained by the set screw 214 so as to be spaced a distance apart from the pin 222. As the housing 204 moves relative to the forked element 200 from the first, uncoupled position to the second, coupled position, the pin 222 can bias against the spring 212. The spring force generated by the biasing of the pin 222 against the spring 212 can assist the housing 204 in moving back into the first, uncoupled position, from the second, coupled position.

With reference to FIGS. 17-19, the actuation member 202 can be coupled to the coupling projection 210 of the forked element 200 and can be manipulated by an operator to move the housing 204 relative to the forked element 200. In this regard, the threads 226 of the actuation member 202 can be threadably coupled to the threads 223 of the coupling projection 210, and the rotation of the actuation member 202 relative to the forked element 200 can result in linear movement of the housing 204 relative to the forked element 200. The actuation member 202 can be composed of any suitable biocompatible material, such as a biocompatible metal, metal alloy, polymer or combination thereof. The actuation member 202 can include a proximal end 240, a distal end 242 and a central bore 244, which can extend from the proximal end 240 to the distal end 242. The plurality of threads 226 can be formed in at least a portion of the central bore 244. In one example, the plurality of threads 226 can be formed in a portion of the central bore 244 adjacent to the proximal end 240, while a remainder of the central bore 244 can be substantially smooth or unthreaded.

The proximal end 240 of the actuation member 202 can include a nut 246, which can extend proximally from the actuation member 202. The nut 246 can be integrally formed with the proximal end 240 of the actuation member 202, or could be mechanically coupled to the proximal end 240, if desired, such as through welding, mechanical fasteners, etc. The nut 246 can allow the operator to use a tool, such as a wrench, to rotate the actuation member 202. In addition, the nut 246 can include a knurl so as to enable the operator to rotate the actuation member 44 by hand. It should be noted, however, that the nut 246 can be optional, as the operator can use a body 202a of the actuation member 202 itself to rotate the actuation member 202 relative to the forked element 200.

The distal end 242 can include a flange 248, which can extend distally from the distal end 242 of the actuation member 202. The flange 248 can define a channel 248a, which can receive a portion of a retaining ring 250. As will be discussed, the retaining ring 250 can couple the actuation member 202 to the housing 204.

With reference to FIGS. 18 and 19, the housing 204 can be coupled to the actuation member 202 via the retaining ring 250 such that the housing 204 can move or translate relative to the forked element 200 upon movement or actuation of the actuation member 202. The housing 204 can include a proximal end 252, the distal end 72, and a central bore 254, which can extend from the proximal end 252 to the distal end 72. The central bore 254 can be sized to enable the housing 204 to move or translate about or relative to the forked element 200.

The proximal end 252 can include a lip 256 and a cross bore 257. The lip 256 can extend proximally from the proximal end 252 to couple the actuation member 202 to the housing 204. In this regard, the lip 256 can have a diameter, which can be greater than a diameter of the flange 248 of the actuation member 202 such that the flange 248 can be received within the lip 256 shown in FIG. 19. The lip 256 can also include a channel 256a, which can receive a portion of the retaining ring 250. With the retaining ring 250 coupled to the lip 256, the flange 248 can be pressed or snapped into engagement with the lip 256 so that the retaining ring 250 can couple the actuation member 202 to the housing 204 for movement relative to the forked element 200. The cross bore 257 can receive the pin 222, which can constrain the movement of the housing 204 relative to the forked element 200, as discussed herein.

The distal end 72 can include the pair of laterally opposed members 72a, 72b, which can be spaced apart to receive the forked element 200 therebetween. The laterally opposed members 72a, 72b can also be coupled together via the extension 73, if desired, to provide additional rigidity to the housing 204. The laterally opposed members 72a, 72b can include a mating tapered surface T, which can cooperate with the taper 208a on the forked element 200 to couple the bone plate 12 to the third plate mounting member 18 when the forked element 200 is in the second, coupled position.

With reference to FIGS. 17-19, the platform 206 can be mounted in a fixed position relative to the forked element 200. In this regard, the platform 206 can be fixedly coupled to the square stem 224a of the platform mounting feature 224 via the square bore 228 (FIG. 19). The platform 206 can be configured to support the targeting arm 19. As the platform 206 can be at a fixed distance relative to the forked element 200, and the forked element 200 does not move relative to the bone plate 12, the distance between the targeting arm 19 and the bone plate 12 can remain constant throughout the surgical procedure. Thus, based on the known distance between the bone plate 12 and the targeting arm 19, the operator can determine the location of the bores 32a-32c, 34a-34c, 36 of the bone plate 12 within the anatomy with minimal use of an imaging device, as will be discussed in greater detail herein. The platform 206 can be composed of any suitable biocompatible material, such as a biocompatible metal, metal alloy, polymer or combinations thereof, for example, carbon fiber. The platform 206 can have a substantially triangular cross-section, and can define a proximal surface 270, a distal surface 272 and can include a throughbore 274, which can extend from the proximal surface 270 to the distal surface 272.

The proximal surface 270 of the platform 206 can support the targeting arm 19. It should be understood, however, that the targeting arm 19 could be supported relative to the bone plate 12 via any suitable technique, such as a slot formed through a portion of the third mounting member 18, by the use of a modular target platform 350, as will be discussed with reference to FIG. 21A.

Generally, the proximal surface 270 can extend along an axis A1, which can be transverse to a longitudinal axis L of the third plate mounting member 18, but substantially parallel to the longitudinal axis L of the bone plate 12. As the proximal surface 270 of the platform 206 can extend in a direction substantially parallel to the longitudinal axis L of the bone plate 12, the targeting arm 19 can also extend in a direction substantially parallel to the longitudinal axis L of the bone plate 12 (FIG. 1). With reference to FIGS. 18 and 19, the proximal surface 270 can include at least one targeting arm locator 276 and can include a coupling bore 278.

The at least one targeting arm locator 276 can provide attachment points for positioning the targeting arm 19 onto the proximal surface 270. In one example, the at least one targeting arm locator 276 can include a first targeting arm locator 276a and a second targeting arm locator 276b. The first targeting arm locator 276a can comprise a substantially cylindrical post or pin, while second targeting arm locator 276b can comprise a diamond shaped post or pin. The use of the diamond-shaped second targeting arm locator 276b can reduce the movement of the targeting arm 19 relative to the platform 206, and can act as a universal locating feature for the targeting arm 19. It should be noted, however, that any suitable shape could be employed for the second targeting arm locator 276b so long as rotation of the targeting arm 19 is substantially minimized. Each of the first targeting arm locator 276a and the second targeting arm locator 276b can extend a predetermined or predefined distance above the proximal surface 270 of the platform 206 to enable the operator to position the targeting arm 19 onto the platform 206.

The coupling bore 278 can be spaced a distance from the first targeting arm locator 276a and the second targeting arm locator 276b, and can be configured to receive a portion of a knob 280 to couple the targeting arm 19 to the platform 206. In one example, the coupling bore 278 can be unthreaded and can receive a post 280a on the knob 280 to couple the targeting arm 19 to the platform 206, as will be discussed in greater detail herein (FIG. 18). It should be noted, however, that the coupling bore 278 could be threaded, and the knob 280 could be optional, and a suitable mechanical fastener could be used to couple the targeting arm 19 to the platform 206.

With reference to FIG. 19, the distal surface 272 of the platform 206 can be angled relative to the proximal surface 270. In this regard, the distal surface 272 can extend along an axis Dp, which can be transverse to both the axis A1 of the proximal surface 270 and the longitudinal axis L of the third plate mounting member 18. By angling the distal surface 272, the nut 246 of the actuation member 202 can be positioned adjacent to the distal surface 272, which can make the actuation member 202 easier to manipulate by the operator.

The throughbore 274 can be substantially parallel to the longitudinal axis L defined by the third plate mounting member 18. The throughbore 274 can include an angled counterbore 274a and the square bore 228. The angled counterbore 274a can receive a head 231a of the mechanical fastener 231, which can be coupled to the plurality of threads 230a of the coupling projection 210 to couple the platform 206 to the forked element 200. The square bore 228 can allow the platform 206 to be positioned onto the coupling projection 210 of the forked element 200 prior to coupling the platform 206 to the forked element 200 via the mechanical fastener 231. It should be noted that instead of or in addition to the mechanical fastener 231, other techniques could be used to couple the platform 206 to the forked element 200, such as adhesives, welding, riveting, etc.

In order to assemble the third plate mounting member 18, the spring 212 can be inserted into the central bore 220 of the forked element 200 and then the set screw 214 can be coupled to the central bore 220 to retain the spring 212 within the forked element 200. Then, the retaining ring 250 can be coupled to one of the actuation member 202 or the housing 204. The housing 204 can be positioned over the proximal end 216 of the forked element 200 and the pin 222 can be inserted through the cross bore 257 of the housing 204 and the slot 216a of the forked element 200. The actuation member 202 can then be positioned such that the threads 226 threadably engage the threads 226 of the forked element 200. The actuation member 202 can be rotated relative to the forked element 200 until the actuation member 202 is coupled to the housing 204 via the retaining ring 250.

With the actuation member 202 and housing 204 coupled to the forked element 200, the platform 206 can be positioned onto the platform coupling member 260. Then, the mechanical fastener 231 can be inserted through the bore 274 of the platform 206 and threadably coupled to the threads 230a of the central bore 220 of the forked element 200.

With the forked element 200 positioned in a first position, the bottom surface 64 of the legs 48 can be positioned onto the bone plate 12 such that the screws S can be received within the location features locators 30a, 30b of the bone plate 12 and the lip 64b can be positioned about the outer edges 41a, 41b of the bone plate 12. From the first position, the actuation member 202 can be rotated by the operator, which can move the forked element 200 from the first position to a second position. In the second position, the housing 204 can be moved or translated onto the forked element 200 such that the taper 228 of the forked element 200 is in contact with the mating taper T of the laterally opposed members 72a, 72b. The contact between the taper 228 and the mating taper T can cause the legs 48 to compress, which in turn can couple or clamp the bone plate 12 to the forked element 200. It should be noted that while the third plate mounting member 18 is coupled to the bone plate 12, each of the bores 32a-32c, 34a-34c, 36 of the bone plate 12 are accessible by the operator.

With the bone plate 12 coupled to the forked element 200, the third plate mounting member 18 can be used to insert the bone plate 12 into the anatomy. With the bone plate 12 inserted into the anatomy, the targeting arm 19 can then be coupled to the platform 206. The targeting arm 19 can enable the operator to determine the location of the bores 32a-32c, 34a-34c, 36 of the bone plate 12 with minimal use of fluoroscopy, as will be discussed in greater detail herein. The third plate mounting member 18 can also be used to bend the bone plate 12 into a desired shape prior to insertion. The third plate mounting member 18 can also be used to remove the bone plate 12 from the anatomy, if desired. Further detail regarding the insertion and removal of a respective bone plate 12 will be discussed in greater detail herein.

Targeting Arm

Figure 20:
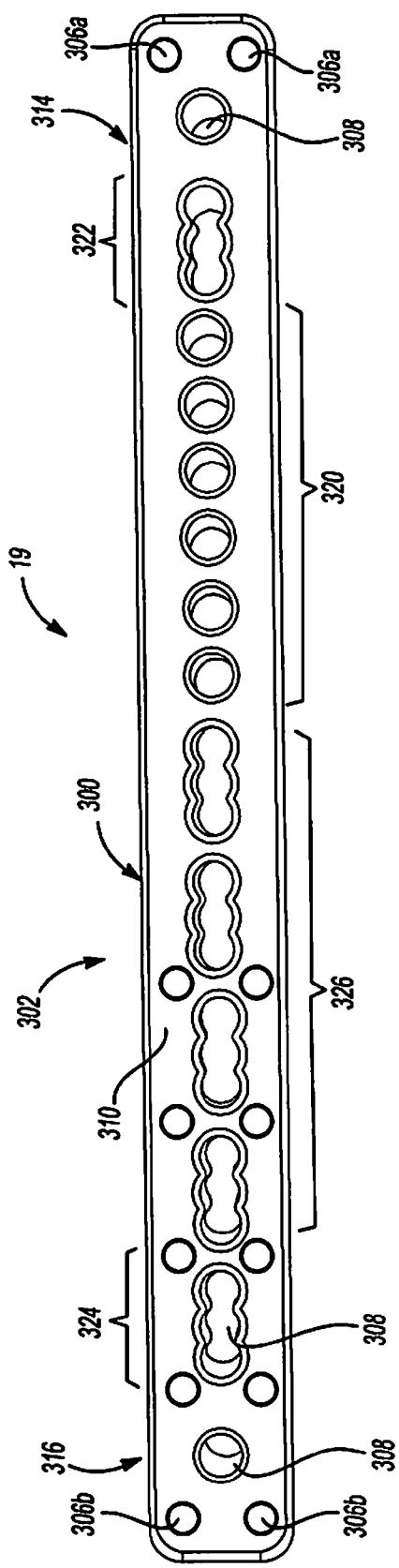
FIG. 20 is a top view of an exemplary targeting arm for use with the system of FIG. 1.
Figure 21:
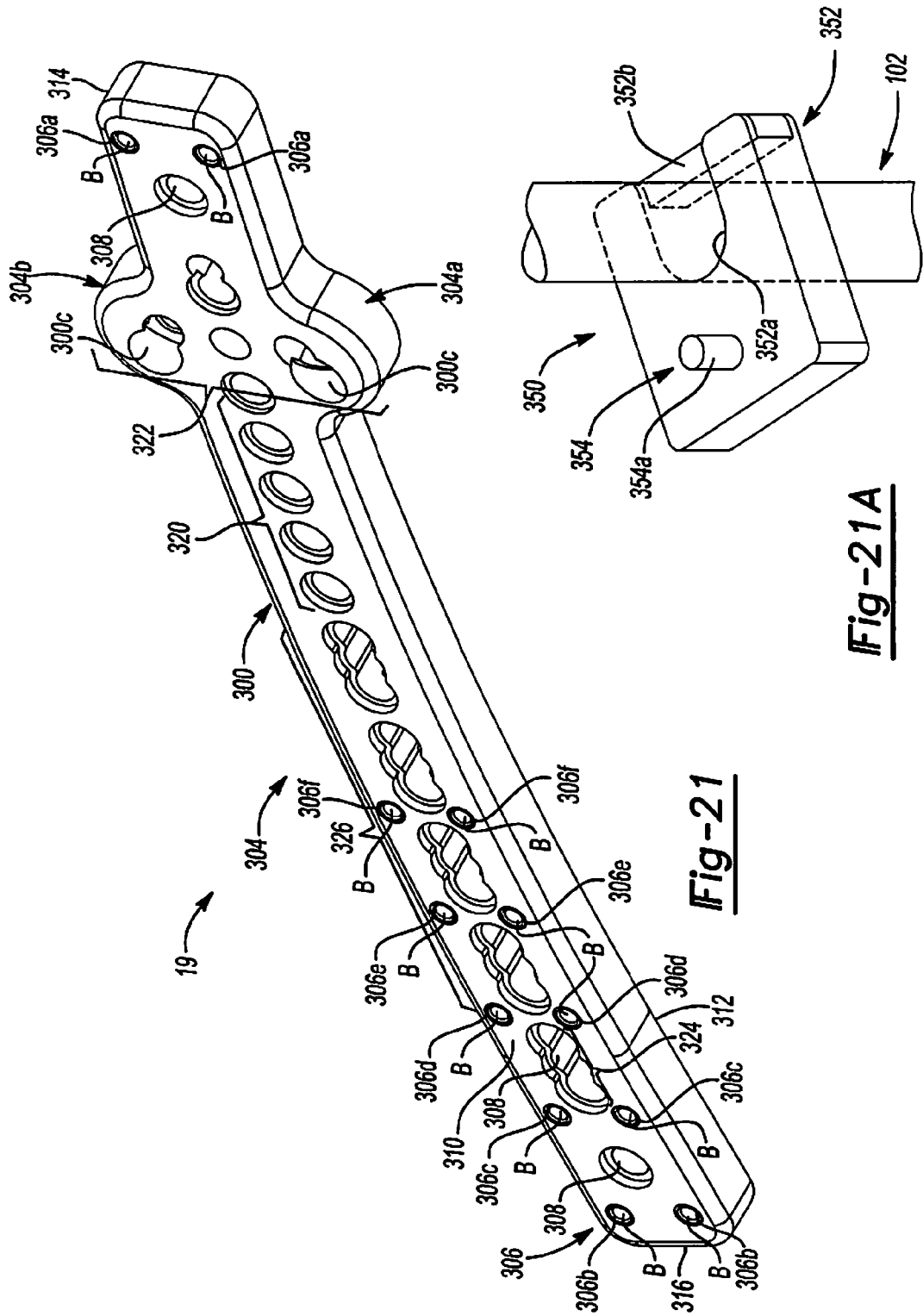
FIG. 21 is a perspective view of another exemplary targeting arm for use with the system of FIG. 1.

With reference to FIGS. 20-21, as discussed, the targeting arm 19 can enable the operator to determine the locations of the bores 32a-32c, 34a-34c, 36 of the bone plate 12 with minimal use of fluoroscopy. In this regard, the targeting arm 19 can include a first plurality of apertures or targeting bores 300, which can be aligned with a respective one of the bores 32a-32c, 34a-34c, 36 of the bone plate 12. As will be discussed, the alignment of the targeting bores 300 with the bores 32a-32c, 34a-34c, 36 of the bone plate 12 can provide the operator with a guide as to the location of the bores 32a-32c, 34a-34c, 36 of the bone plate 12 with minimal use of fluoroscopy or other imaging techniques.

With reference to FIG. 20, the targeting arm 19 can comprise a straight targeting arm 302, which can have targeting bores 300 that correspond with the bores 32a-32c, 34a-34c, 36 of the straight plate 22. The targeting arm 19 can also comprise a flared targeting arm 304, as shown in FIG. 21, which can have targeting bores 300 that correspond with the bores 32a-32c, 34a-34c, 36 of the right flared plate 24 and the left flared plate 26. It should be noted that although the targeting arms 302, 304 are described herein as corresponding to the bone plates 12, it will be understood that the targeting arms 302, 304 can be used with any suitable submuscular bone plate, and can be used with submuscular bone plates having lengths different from the bone plates 12, as will be discussed herein. The targeting arms 302, 304 can be formed of a suitable biocompatible material, such as a biocompatible metal, metal alloy or polymer, for example, carbon fiber.

It should be noted that with regard to the flared targeting arm 304, as illustrated in FIG. 21, in one example, the targeting bores 300 on a first side 310 of the flared targeting arm 304 can correspond to the bores 32a-32c, 34a-34c, 36 of the right-flared plate 26, while the targeting bores 300 on a second side 312 of the targeting arm 304 can correspond to the bores 32a-32c, 34a-34c, 36 of the left-flared plate 24. In one example, a first or proximal end 314 of the first side 310 of the targeting arm 304 can correspond to the proximal end 28 of the right flared plate 26, while the proximal end 314 of the second side 312 can correspond to the distal end 30 of the left flared plate 24.

The flared targeting arm 304 can include at least one or a plurality of wings 304a, 304b. The wings 304a, 304b can include a first bore 300c, which can correspond with the bore 32c or bore 34c of the bone plate 12 depending upon the length of the bone plate 12 and the insertion technique employed with the bone plate 12, as will be discussed herein. The flared targeting arm 304 can also have a bow radius. The bow radius can be defined between a straight portion ST associated with the proximal end 312 and a straight portion ST associated with the distal end 314 of the bone plate 12. The bow radius can have any suitable curvature that enables the flared targeting arm to correspond with the left flared plate 24 and the right flared plate 26, such as about 50 inches (in) in the case of a pediatric femur. The straight portions ST of the proximal end 312 and the distal end 314 can enable the targeting arm 304 to be coupled to the third plate mounting member 18 at either end.

It should be understood that the use of a single flared targeting arm 304 for either of the left-flared plate 24 or right-flared plate 26 is merely exemplary, as two flared targeting arms, one corresponding to each of the left-flared plate 24 and right-flared plate 26, could be employed if desired. Further, an exemplary targeting arm 19 could have a "duckbill" shape with targeting bores formed along the length of the "duck-bill" that correspond to both the left-flared plate 24 and the right-flared plate 26. As another example, the targeting arm 19 could be modular, with a common base and a plurality of attachments. Each of the plurality of attachments could define targeting bores that correspond to a particular bone plate 12 and could be coupled to the base to enable the targeting arm to be used with a desired bone plate 12. In addition, the targeting arm could include a sliding targeting guide, which could be movably coupled along a surface of the targeting arm to provide a path for guiding an additional fixation device into the anatomy.

Each of the targeting arms 302, 304 can include the targeting bores 300, a second plurality of apertures or mounting bores 306 and at least one or a plurality of coupling bores 308. The targeting bores 300, mounting bores 306 and coupling bores 308 can extend through the targeting arms 302, 304 from the first side 310 to the second side 312. The targeting bores 300, mounting bores 306 and coupling bores 308 can be formed along the targeting arms 302, 304 so as to extend from the proximal end 314 of the targeting arms 302, 304 to the distal end 316 of the targeting arms 302, 304.

The targeting bores 300 can each be formed about a centerline, and can each include a plurality of threads if desired. For example, a plurality of threads can extend through each of the targeting bores 300 from the first side 310 to the second side 312. It should be understood, however, that the plurality of threads can extend partially through each of the targeting bores 300, if desired. As the targeting bores 300 can be formed to correspond to the bores 32a-32c, 34a-34c, 36 of the bone plate 12, in one example, a first subset 320 of the targeting bores 300 can be defined through the targeting arms 302, 304 to correspond with the portion of the bores 36 of the bone plate 12, a second subset 322 of the targeting bores 300 can be defined to correspond with the first plurality of cluster bores 32a-32c of the bone plate 12 and/or the second plurality of cluster bores 34a-34c, a third subset 324 of the targeting bores 300 can be defined to correspond with the second plurality of cluster bores 34a-34c, a fourth subset 326 of the targeting bores 300 can be defined to correspond with a remainder of the plurality of bores 36 and/or the first plurality of cluster bores 32a-32c, as will be discussed herein. With reference to FIG. 1, an imaginary targeting line LT can extend from each of the targeting bores 300 to the respective bore 32a-32c, 34a-34c, 36 of the bone plate 12. With regard to the first bore 300c of the flared targeting arm 304, an imaginary targeting line LT can also be created to extend from the first bore 300c to the bores 32c or 34c of the bone plate 12.

With reference to FIGS. 20 and 21, the first subset 320 of the targeting bores 300 can comprise individual bores defined between the proximal end 314 and the distal end 316 of the targeting arms 302, 304. In one example, the centerline associated with each of the targeting bores 300 in the first subset 320 can be coaxially aligned with a centerline of a subset of the bores 36a-36e of the bone plate 12 such that an imaginary targeting line LT can extend from each of the targeting bores 300 in the first subset 320 to the respective subset the bores 36 of the bone plate 12. It should be noted that although the first subset 320 is described and illustrated herein as corresponding to only a portion of the plurality of bores 36, it will be understood that if desired, the first subset 320 could correspond to all of the plurality of bores 36.

The second subset 322 of the targeting bores 300 can be defined near or at the proximal end 314 of the targeting arms 302, 304. The centerline associated with each of the targeting bores 300 in the second subset 322 can be coaxially aligned with a centerline of each of the first plurality of cluster bores 32a-32c of the bone plate 12 when a full-length bone plate 12 is used and the bone plate 12 is inserted from the hip. An imaginary targeting line LT can extend from each of the targeting bores 300 in the second subset 322 to each of the first plurality of cluster bores 32a-32c of the bone plate 12.

It should be noted that in the case of a bone plate 12 inserted into the anatomy from the knee, the second subset 322 of the targeting bores 300 can be coaxially aligned with a centerline C of each of the plurality of second cluster bores 34a-34c of the bone plate 12. In other words, as will be discussed in greater detail herein, if it is desirable to insert the bone plate 12 from the knee, the respective plate mounting member 14, 16, 18 can be coupled to the distal end 316 of the targeting arms 302, 204, and the second subset 322 of the targeting bores 300 can be coaxially aligned with the second plurality of cluster bores 34a-34c of the bone plate 12.

The third subset 324 of the targeting bores 300 can be defined can be defined near or at the distal end 316 of the targeting arms 302, 304 to correspond with the second plurality of cluster bores 34a-34c in the case of a full-length bone plate 12 inserted from the hip. In the case of a full-length bone plate 12 inserted from the hip, the centerline associated with each of the targeting bores 300 in the third subset 324 can be coaxially aligned with a centerline of each of the second plurality of cluster bores 34a-34c of the bone plate 12 such that an imaginary targeting line LT can extend from each of the targeting bores 300 in the third subset 324 to each of the second plurality of cluster bores 34a-34c of the bone plate 12. In the case of a bone plate 12 inserted from the knee, the third subset 324 of targeting bores 300 may be coaxially aligned with a centerline of each of the first plurality of cluster bores 32a-32c of the bone plate 12.

The fourth subset 326 of the targeting bores 300 can be defined to correspond with a remainder of the plurality of bores 36 in the case of a full-length plate 12 or the first plurality of cluster bores 32a-32c in the case of a less than full-length plate 12. The fourth subset 326 of targeting bores 300 can be defined near or at the distal end 316 of the targeting arms 302, 304. The centerline associated with each of the targeting bores 300 in the fourth subset 326 can be coaxially aligned with a centerline of each of the remainder of the plurality of bores 36 of the full-length plate 12 or the plurality of cluster bores 32a-32c of a less then full-length plate 12 such that an imaginary targeting line LT can extend from each of the targeting bores 300 in the fourth subset 326 to each of the bores 36 of the bone plate 12 or the plurality of cluster bores 32a-32c of a less than full-length plate, as will be discussed in greater detail herein.

The mounting bores 306 can be formed at the proximal end 314 and at or near the distal end 316 of the targeting arms 302, 304. The mounting bores 306 can be configured to mate with the targeting arm locators 276a, 276b of the platform 206. Thus, the mounting bores 306 can be defined through the targeting arms 302, 304 as pairs of substantially cylindrical apertures, and in one example, the mounting bores 306 can comprise a first pair of mounting bores 306a, a second pair of mounting bores 306b, a third pair of mounting bores 306c, a fourth pair of mounting bores 306d, a fifth pair of mounting bores 306e and a sixth pair of mounting bores 306f. Each of the pairs of mounting bores 306a-306f can receive the targeting arm locators 276a, 276b to allow the targeting arms 302, 304 to be used with bone plates 12 of various lengths. In addition, when not in use, bushings B can be inserted into each of the mounting bores 306 to preserve the integrity of the mounting bores 306. It should be noted, however, that the bushings B can be optional or unnecessary if other attachment techniques are utilized to couple the targeting arm 19 to the plate mounting member (14, 16, 18).

In the case of a full-length bone plate 12 inserted from the hip, the third plate mounting member 18 can be coupled to the first pair of mounting bores 306a. In the case of a full-length bone plate 12 inserted from the knee, the targeting arm locators 276a, 276b of the third plate mounting member 18 can be coupled to the second pair of mounting bores 306b. In a further example, in the case of a reduced length bone plate 12, such as a 16 hole plate, the targeting arm locators 276a, 276b of the third plate mounting member 18 can be coupled to the third pair of mounting bores 306c. In the case of a 14 hole plate, the targeting arm locators 276a, 276b of the third plate mounting member 18 can be coupled to the fourth pair of mounting bores 306d. As a further example of a reduced length plate, such as a 12 hole plate, the targeting arm locators 276a, 276b of the third plate mounting member 18 can be coupled to the fifth pair of mounting bores 306e. In the case of a 10 hole plate, the targeting arm locators 276a, 276b of the third plate mounting member 18 can be coupled to the sixth pair of mounting bores 306f.

The coupling bores 308 can be defined from the proximal end 314 to the distal end 316 of the targeting arms 302, 304. The coupling bores 308 can be configured to receive the post 280a of the knob 280 therethrough to couple the targeting arms 302, 304 to the third plate mounting member 18 via the knob 280. As the targeting arms 302, 304 can be utilized with bone plates 12 of varying lengths, the coupling bores 308 can be defined adjacent to the mounting bores 306a-306f so that the respective coupling bore 308 of the targeting arms 302, 304 can be coaxially aligned with the coupling bore 278 of the third plate mounting member 18 to facilitate the engagement of the knob 280 with the coupling bore 278.

The targeting arms 302, 304 can be employed with the third plate mounting member 18 and/or a portion of the anchoring system 20 and can provide an imaginary targeting line between the mounting bores 306 and the bores 32a-32c, 34a-34c, 36 of the bone plate 12 to enable the insertion of the bone fastener 40 into the anatomy and the bone plate 12 (FIG. 1). In addition, the targeting arms 302, 304 can be employed with the first plate mounting member 14 and the second plate mounting member 16 through the modular target platform 350, illustrated in FIG. 21A.

With continued reference to FIG. 21A, the modular target platform 350 support the targeting arm 19 relative to the bone plate 12 on the first plate mounting member 14 and second plate mounting member 16. The modular target platform 350 can be formed of a suitable biocompatible material, such as a biocompatible metal, metal alloy or polymer, for example, a carbon fiber. In one example, the modular target platform 350 can include a base 352 and a coupling feature 354. The base 352 can be substantially U-shaped, and can define an aperture 352a. The aperture 352a can be configured to receive a portion of the first plate mounting member 14 and second plate mounting member 16 therethrough to couple the modular target platform 350 to the first plate mounting member 14 and second plate mounting member 16.

Generally, the base 352 can be configured to be fixedly coupled to the portion of the first plate mounting member 14 and second plate mounting member 16. In one example, the aperture 352a can be contoured to frictionally engage the first plate mounting member 14 and second plate mounting member 16. Alternatively, the base 352 can include a clamping arm 352b, which can be configured to secure or fix the base 352 to the housing 46 of the first plate mounting member 14 and the housing 101 of the second plate mounting member 16.

The coupling feature 354 can extend proximally or upwardly from the base 352, and can couple the modular target platform 350 to the targeting arm 19. In one example, the coupling feature 354 can include a post 354a, which can be configured to pass through a coupling bore 308 of the targeting arm 19. A locking knob can be coupled to a portion of the post 354a that extends beyond the first side 310 of the targeting arm 19 to further secure the targeting arm 19 to the modular target platform 350, if desired.

Anchoring Assembly

The anchoring system 20 can be used with the bone plate 12 to repair a damaged portion of an anatomy. The anchoring system 20 can include a guidewire 400, a locking wire guide 402, a screw insertion instrument 404 and the bone fastener 398. The guidewire 400 can comprise any suitable guidewire known in the art, and can be inserted along the imaginary targeting line TL to provisionally identify the location of the bores 32a-32c, 34a-34c, 36 of the bone plate 12 relative to the anatomy.

The locking wire guide 402 can be cannulated so as to be passed over the guidewire 400. In one example, the locking wire guide 402 can include a tubular body 406 and a support block 408. The tubular body 406 can include a proximal end 410 and a distal end 412. The proximal end 410 can include a plurality of threads 410a, and can be sized to be received through a coupling bore 308 of the targeting arm 19 so that the targeting arm 19 can be coupled to the locking wire guide 402, if desired. In this regard, the plurality of threads 410a can be configured to enable a locking knob 414 with a threaded bore 414a to be coupled to the proximal end 410 of the locking wire guide 402. The locking knob 414 can couple the targeting arm 19 to the locking wire guide 402, which may be desirable in surgical procedures not involving the use of the third plate mounting member 18, for example, as will be discussed in greater detail herein.

The distal end 412 of the tubular body 406 can be configured to be coupled to the bores 32a-32c, 34a-34c, 36 of the bone plate 12. In one example, the distal end 412 can include a plurality of threads 412a. The plurality of threads 412a can mate with the plurality of threads 38a disposed about the bores 32a-32c, 34a-34c, 36 of the bone plates 12 to couple or lock the tubular body 406 to the bone plate 12. It should be noted, however, that the distal end 412 of the tubular body 406 can be unthreaded, and can be pushed into or snapped into engagement with the bores 32a-32c, 34a-34c, 36 of the bone plate 12. In addition, it will be understood that although a locking wire guide 402 is described herein that locks to the bone plate 12, a non-locking wire guide could be employed, if desired.

The support block 408 can be disposed about the tubular body 406. In one example, the support block 408 can be slidably disposed about the tubular body 406 so as to be movable as desired between the proximal end 410 and the distal end 412 of the tubular body 406. The support block 408 can comprise a platform for supporting the targeting arm 19 relative to the bone plate 12. It should be noted, however, that the support block 408 can be optional. In addition, the support block 408 can include at least one or a pair of opposing scallops 408a, 408b, which can provide access to the bores 32a-32c, 34a-34c, 36 of the bone plate 12. For example the scallops 408a, 408b can enable the screw insertion instrument 404 to engage the respective bore 32a-32c, 34a-34c, 36 on either side of the locking wire guide 402.

The screw insertion instrument 404 can drive the bone fastener 398 into engagement with the anatomy and can also couple the bone fastener 398 to the respective bore 32a-32c, 34a-34c, 36 of the bone plate 12. The screw insertion instrument 404 can comprise any suitable screw insertion instrument that can be used to drive the bone fastener 398 into engagement with the anatomy and the bone plate 12. In one example, an exemplary screw insertion instrument can include those disclosed in commonly owned PCT International Publication No. PCT/US2008/080178, filed on Oct. 16, 2008 and incorporated by reference herein. As the screw insertion instrument 404 can comprise any suitable instrument known in the art, the screw insertion instrument 404 will not be discussed in detail herein. Briefly, however, the screw insertion instrument 404 can include a locking connector shaft 420, which can extend through a cannulated body 422, and a driver tip 424.

In one example, the locking connector shaft 420 can extend through the body 422, and can include a proximal end 426 and a distal end 428. The proximal end 426 can be positioned next to a handle 430 coupled to the body 422, and can also comprise a graspable portion 426a, which can enable the locking connector shaft 420 to be rotatable relative to the body 422. The distal end 428 can include a plurality of threads 428a, which can engage or lock the bone fastener 398 to the screw insertion instrument 404, as will be discussed herein.

The driver tip 424 can be formed about a distal end 434 of the body 422, and can be configured to engage a head 436 of the bone fastener 398. In this example, the driver tip 424 can comprise a hexalobe driver, which can mate with a corresponding hexalobe receiving portion 438 defined in the head 436 of the bone fastener 398, as shown in FIGS. 23 and 24.

The bone fastener 398 can be composed of any suitable biocompatible material, such as a metal, metal alloy or polymer, and if desired, can be coated with a growth agent, antibiotic, etc. to assist in coupling the bone fastener 398 to the anatomy. It should be noted that the bone fastener 398 can comprise any suitable bone fastener that cooperates with the screw insertion instrument 404 to engage the anatomy and the bone plate 12, and in one example, the bone fastener could comprise one of the bone fasteners disclosed in commonly owned PCT International Publication No. PCT/US2008/080178, filed on Oct. 16, 2008 and incorporated by reference herein. As the bone fastener 398 can comprise any suitable bone fastener known in the art, the bone fastener 398 will not be discussed in detail herein. Briefly, however, the bone fastener 398 can include the head 436, which can define the hexalobe receiving portion 438 and a threaded locking portion 440, and a shank 442.

The head 436 can include an exterior surface 444, having the plurality of threads 398a, and an interior surface 446, which can include the hexalobe receiving portion 438 and a threaded locking portion 440. The hexalobe receiving portion 438 can be defined near a proximal end 436a of the head 436, while the threaded locking portion 440 can be defined at a distal end 436b of the head 436. The hexalobe receiving portion 438 can mate with the driver tip 424 of the screw insertion instrument 404 to enable the screw insertion instrument 404 to drive the bone fastener 398 into the anatomy. The threaded locking portion 440 can mate with the plurality of threads 438a of the locking connector shaft 420 to couple or lock the bone fastener 398 to the screw insertion instrument 404. It should be noted, however, that the driver tip 424 of the screw insertion instrument 404 can enable the bone fastener 398 to be couple to the screw insertion instrument 404 through the application of force (e.g. "stab and grab").

The shank 442 of the bone fastener 398 can comprise a plurality of threads 442a and can include one or more cutting flutes 442b. The plurality of threads 442a and the cutting flutes 442b can cooperate to drive the bone fastener 398 into the anatomy. In addition, the shank 442 can include two minimum diameters for strength.

With reference back to FIG. 1, in order to repair a damaged portion of the anatomy using the submuscular plating system 10, surgical access can be made through the skin adjacent to the femoral bone fragments F. The specific surgical access approaches are beyond the scope of the present application, but for example, surgical access can be obtained via a minimally invasive surgical procedure or an open surgical procedure, as generally known in the art. With access gained to the anatomy, a plate mounting member 14, 16, 18 can be coupled to a desired bone plate 12. The plate mounting member 14, 16, 18 can be used to manipulate the bone plate 12 and insert the bone plate 12 into the anatomy. Alternatively, the locking wire guide 402 can be coupled to the bone plate 12 to enable the surgeon to manipulate the bone plate 12 and insert the bone plate 12 into the anatomy. The bone plate 12 can be inserted via an antegrade approach, from the hip, or through a retrograde approach, from the knee.

Figure 25A:
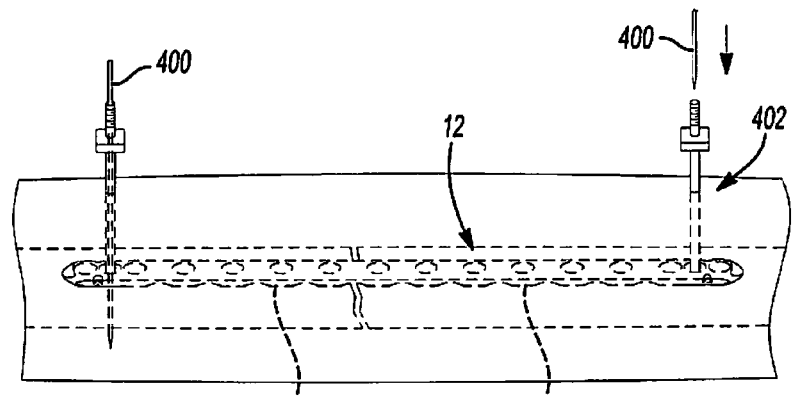
FIG. 25A is a schematic environmental illustration of a first portion of an exemplary method of using the system of FIG. 1.

With the bone plate 12 inserted into the anatomy, the surgeon can constrain the bone plate 12 relative to the anatomy. In one example, with reference to FIGS. 25A-25C, the locking wire guide 402 coupled to one end of the bone plate 12, a suitable imaging device, such as a fluoroscope, can be utilized during the surgical procedure to facilitate locating the bores 32a-32c, 34a-34c, 36 at the opposing end of the bone plate 12 within the anatomy. Then, a guidewire 400 can be inserted through the anatomy, through the opposing bore 32a-32c, 34a-34c, 36 and into a corresponding bone fragment F. A second locking wire guide 402 can be inserted over the guidewire 400, and coupled to the bone plate 12 (FIG. 25A). The guidewire 400b can cooperate with the locking wire guide 402 to constrain the opposing end of the bone plate 12. Next, the locking wire guide 402 at the free or unconstrained end can be moved in a direction toward the constrained end of the bone plate 12 to reduce the fracture between the bone fragments F. Once the fracture is reduced, a second guidewire 400 can be inserted through the locking wire guide 402 to constrain the free end of the bone plate 12 (FIG. 25A).

Figure 25B:
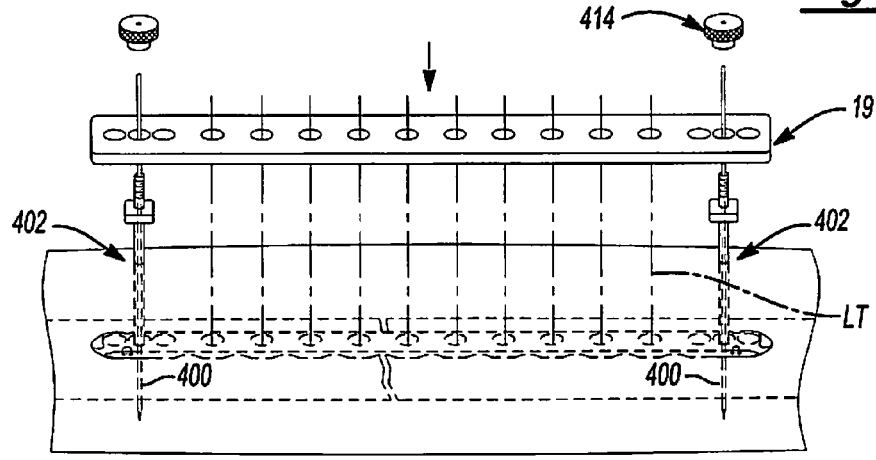
FIG. 25B is a schematic environmental illustration of another portion of the exemplary method of FIG. 25A.
Figure 25C:
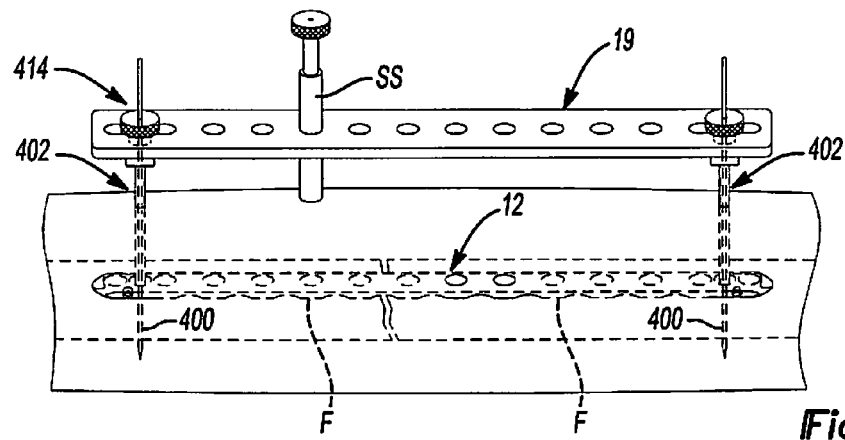
FIG. 25C is a schematic environmental illustration of another portion of the exemplary method of FIG. 25A.

With both ends of the bone plate 12 constrained relative to the anatomy, the targeting arm 19 can be positioned over the locking wire guides 402 to rest on the support 408 (FIG. 25B).

The targeting arm 19 can be coupled to the locking wire guides 402 via at least one locking knob 414 such that the targeting arm 302 is fixed relative to the bone plate 12.

Figure 26A:
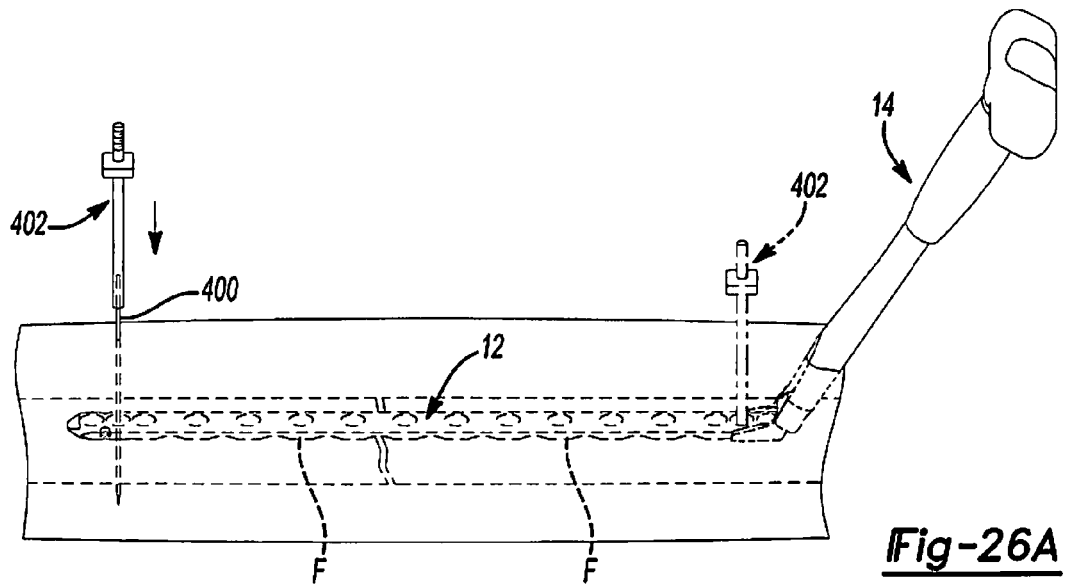
FIG. 26A is a schematic environmental illustration of a first portion of another exemplary method of using the system of FIG. 1.
Figure 26B:
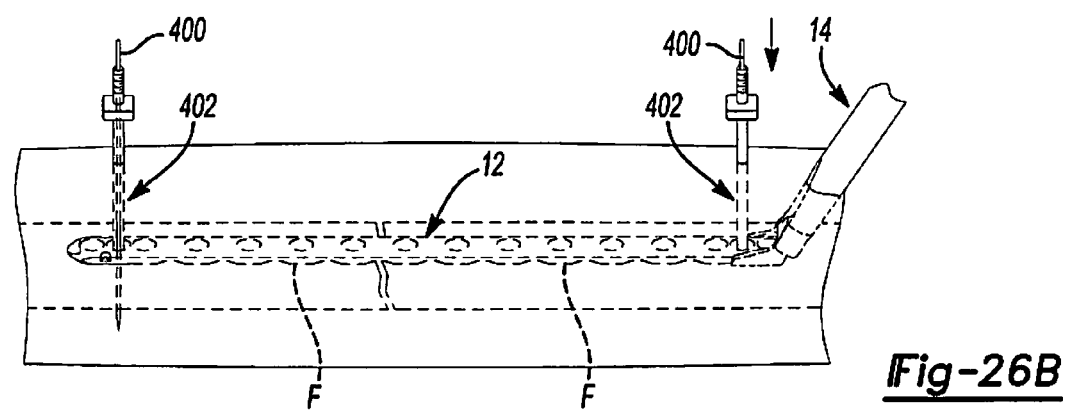
FIG. 26B is a schematic environmental illustration of another portion of the exemplary method of FIG. 26A.
Figure 26C:
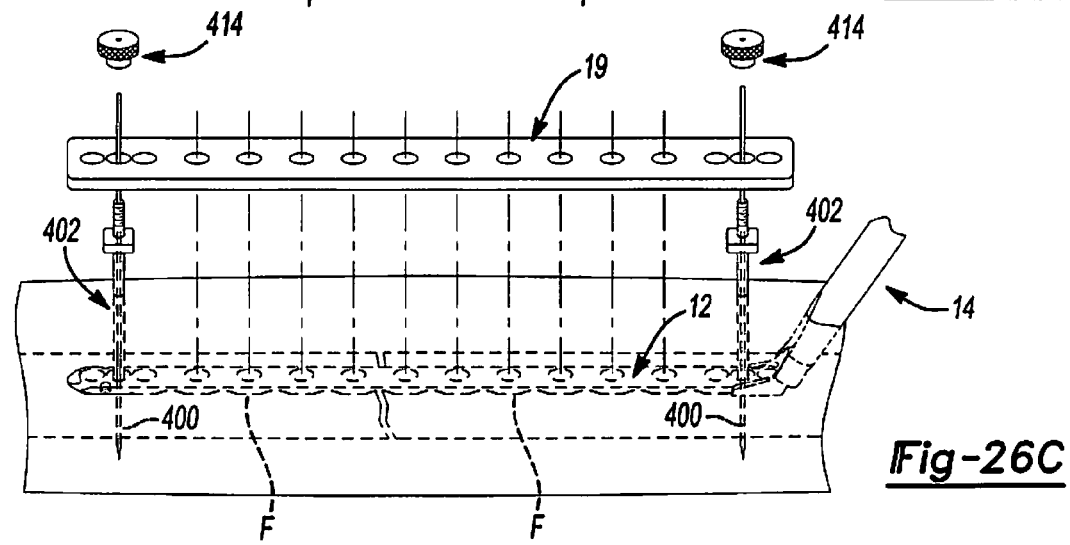
FIG. 26C is a schematic environmental illustration of another portion of the exemplary method of FIG. 26A.

In another example, with reference to FIGS. 26A-26C, the first plate mounting member 14 or second plate mounting member 16 can be coupled to an end of the bone plate 12, and used to insert the bone plate 12 into the anatomy. In this example, a suitable imaging device, such as a fluoroscope, can be utilized during the surgical procedure to facilitate locating the bores 32a-32c, 34a-34c, 36 of at an opposing end of the bone plate 12 within the anatomy. Once the opposing bore 32a-32c, 34a-34c, 36 have been located, a guidewire 400 can be inserted through the opposing bore 32a-32c, 34a-34c, 36 and into a corresponding bone fragment F (FIG. 26A). Then, a locking wire guide 402 can be inserted into the anatomy over the guidewire 400 and the distal end 412 of the locking wire guide 402 can be coupled to the respective bore 32a-32c, 34a-34c, 36 of the bone plate 12. The locking wire guide 402 and the guidewire 400 can serve to constrain the opposing end of the bone plate 12 relative to the anatomy. With the opposing end of the bone plate 12 constrained, the first plate mounting member 14 or second plate mounting member 16 can move the free end of the bone plate 12 towards the constrained opposed end of the bone plate 12 to reduce the fracture.

With the reduction established, with reference to FIG. 26B, a second guidewire 400 can be inserted through a bore 32a-32c, 34a-34c, 36 of the bone plate 12 adjacent to the first plate mounting member 14 or second plate mounting member 16 and into the bone fragment F. A second locking wire guide 402 can then be introduced over the second guidewire 400 and coupled to the bone plate 12 to constrain the end of the bone plate 12 adjacent to the first plate mounting member 14 or second plate mounting member 16. It should be noted that the second locking wire guide 402 can be coupled to the bone plate 12 adjacent to the first plate mounting member 14 or second plate mounting member 16 prior to the insertion of the bone plate 12 to reduce procedure time. In this example, the second guidewire 400 can be passed through the locking wire guide 402 once the fracture has been reduced.

With the bone plate 12 constrained to the anatomy, the targeting arm 19 can be coupled relative to the bone plate 12, if desired (FIG. 26C). In one example, the targeting arm 19 can be coupled relative to the bone plate 12 by positioning the targeting arm 19 over the locking wire guides 402 and onto the support blocks 408. The targeting arm 19 can then be secured to the locking wire guides 402 via the use of at least one locking knob 414, for example. Alternatively, one end of the targeting arm 19 could be coupled to the locking wire guide 402 at the opposing end and then the modular target platform 350 (FIG. 21A) could be used to couple the other end of the targeting arm 19 to the first plate mounting member 14 or second plate mounting member 16. A locking knob 414 can then be coupled to at least the coupling feature 354 of the modular target platform 350 to fix the targeting arm 19 relative to the bone plate 12.

Figure 27A:
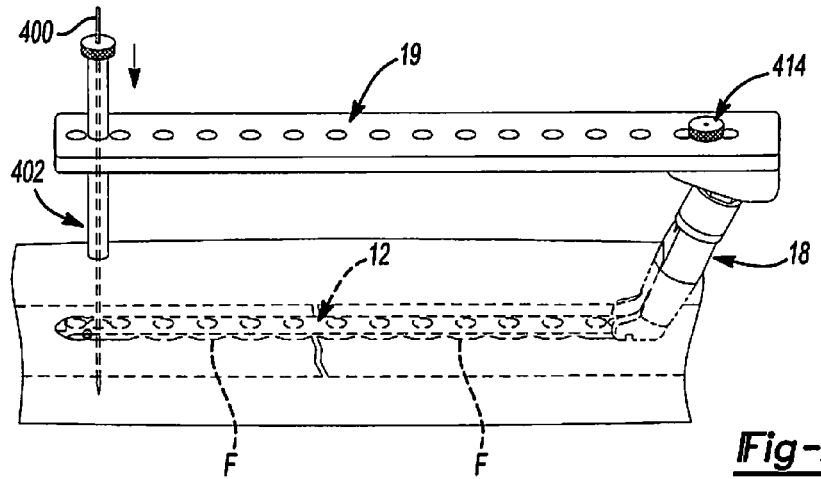
FIG. 27A is a schematic environmental illustration of a first portion of another exemplary method of using the system of FIG. 1.
Figure 27B:
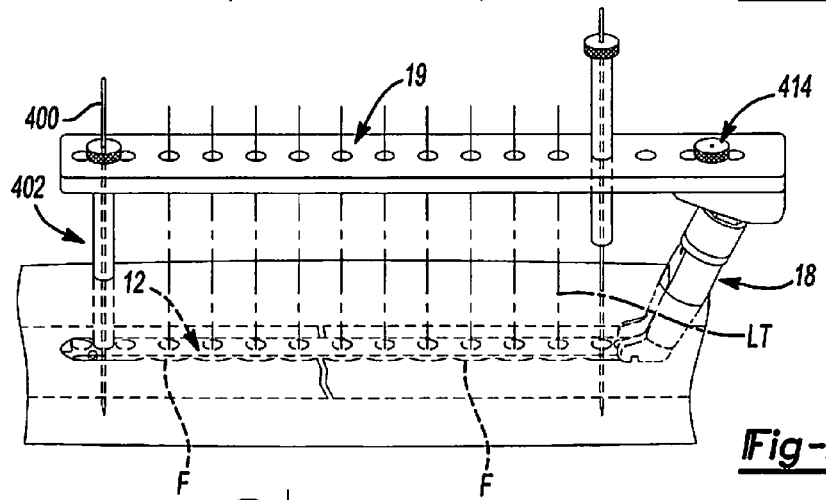
FIG. 27B is a schematic environmental illustration of another portion of the exemplary method of FIG. 27A.
Figure 27C:
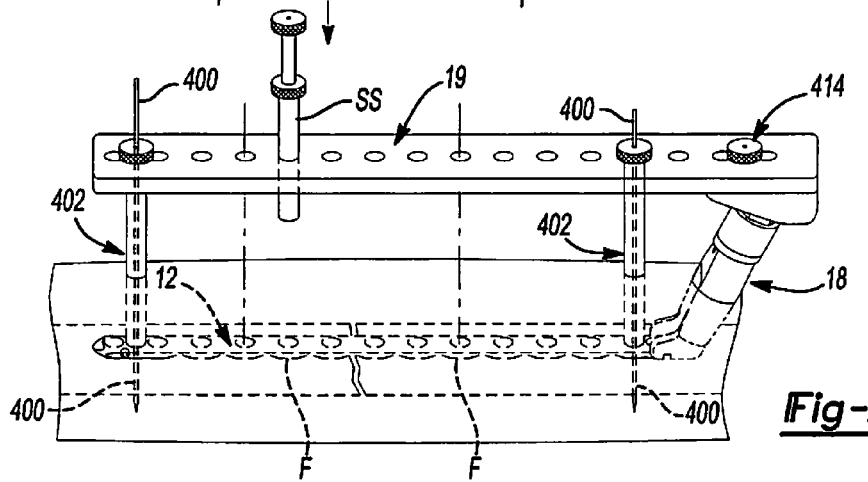
FIG. 27C is a schematic environmental illustration of another portion of the exemplary method of FIG. 27A.
Figure 28:
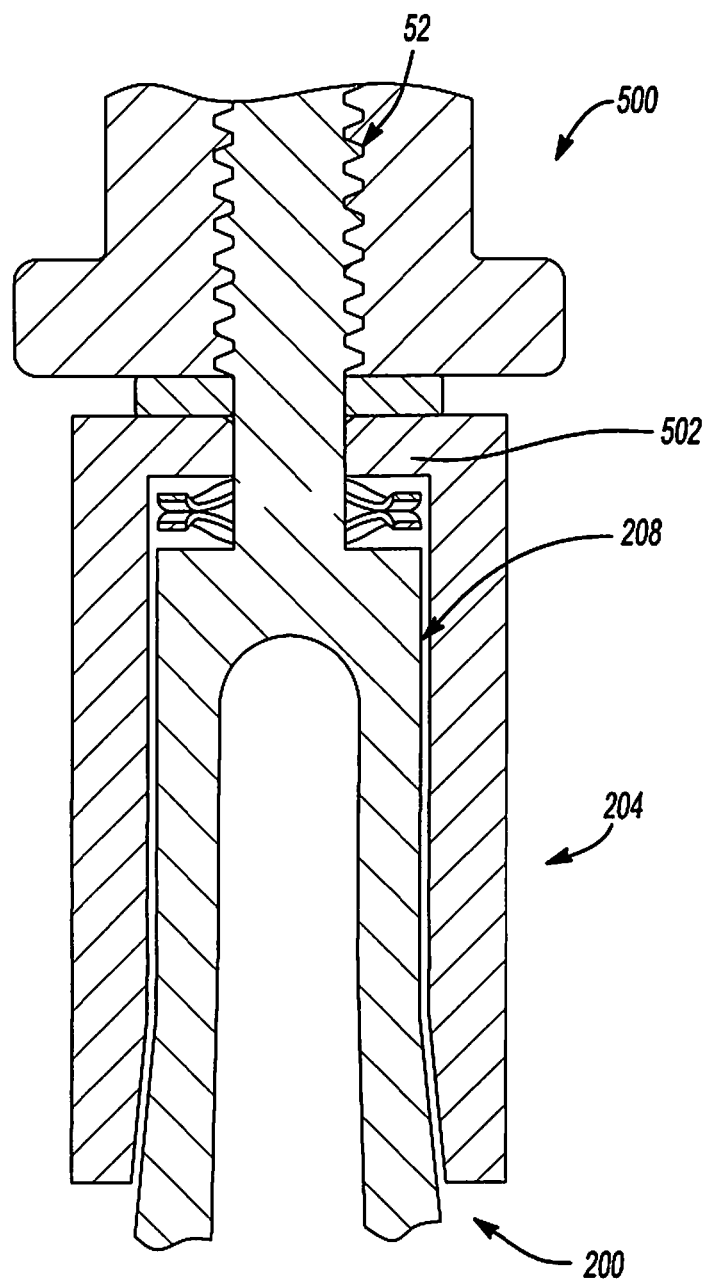
FIG. 28 is a side, partially cut-away schematic illustration of another exemplary plate mounting member for use with the submuscular plate system of FIG. 1.

With regard to the third plate mounting member 18, with reference to FIGS. 27A-27C, the third plate mounting member 18 can be coupled to one end of the bone plate 12, and can be manipulated by the surgeon to insert the bone plate 12 into the anatomy. In one example, the targeting arm 19 can be coupled to the third plate mounting member 18 prior to the insertion of the bone plate 12 into the anatomy. In this example, the targeting arm 19 and the imaging device can be employed to identify the bores 32a-32c, 34a-34c, 36 on the opposing end of the bone plate 12. Then, a guidewire 400 can be inserted through the bore 32a-32c, 34a-34c, 36 on the opposing end of the bone plate 12 and into the anatomy (FIG. 27A). A locking wire guide 402 can be inserted over the guidewire 400 and coupled to the bone plate 12 to constrain the opposed end of the bone plate 12 to the anatomy.

Then, the third plate mounting member 18 can be moved relative to the constrained end of the bone plate 12 to reduce the fracture. With the fracture reduced, a second guidewire 400 can be inserted through the targeting arm 19 and a bore 32a-32c, 34a-34c, 36 of the bone plate 12 adjacent to the third plate mounting member 18 to constrain or fix the end of the bone plate 12 coupled to the third plate mounting member 18 relative to the anatomy (FIG. 27B). A second locking wire guide 402 can be inserted over the second guidewire 400 to constrain the bone plate 12 and the targeting arm 19 relative to the anatomy, With the targeting arm 19 and bone plate 12 constrained relative to each other and relative to the anatomy, the surgeon can begin to repair the damaged portion of the anatomy. It should be noted that the surgeon can use any suitable technique or instruments to repair the damaged anatomy, such as the use of additional guidewires 400, drills, soft tissue sleeves SS (FIGS. 25C, 27C), etc. Exemplary instruments for use to repair a damaged portion of the anatomy can be commercially available from Biomet, Inc. of Warsaw, Ind., or can include those disclosed in commonly owned PCT International Publication No. PCT/US2008/080178, filed on Oct. 16, 2008, and previously incorporated by reference herein. Once the surgeon has prepared the anatomy to receive the bone fastener 398, the screw insertion instrument 404 can be coupled to the bone fastener 398 by mating the threaded locking portion 440 with the plurality of threads 438a of the locking connector shaft 420 and the hexalobe receiving portion 438 with the driver tip 424. Then, the screw insertion instrument 404 can be used to drive the bone fastener 398 into the anatomy.

Accordingly, the submuscular plating system 10 can be used to repair damaged tissue in the anatomy, such as in the case of a femoral fracture fixation procedure. By providing various plates 12, plate mounting members 14, 16, 18 and targeting arms 19, the surgeon can tailor the procedure to the patient, thereby allowing the submuscular plating system 10 to be employed with a variety of different anatomical structures. The various components of the submuscular plating system 10 can also provide the operator with a variety of available techniques to "close the box" or constrain the bone plate 12 and targeting arm 19 relative to the anatomy. Further, the use of the targeting arm 19 can allow the surgeon to minimize the use of an imaging device during the procedure. In addition, if desired, various components of the submuscular plating system 10 can be color coded, if desired, to indicate whether the device is orientated for use with a left or a right flared bone plate 24, 26.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

For example, while the third plate mounting member 18 has been described herein with reference to FIGS. 17-19 as including the housing 204 in direct contact with the forked element 200 in the second position, those of skill in the art will appreciate that the present disclosure, in its broadest aspects, may be constructed somewhat differently. In this regard, with reference to FIG. 26, a third plate mounting member 500 could include a wave washer 502 disposed about the coupling projection 210 of the forked element 200 so as to be positioned between the housing 204 and the base 208 of the forked element 200. The wave washer 502 can allow for provisional tightening of the housing 204 relative to the forked element 200, which can allow the operator to ensure that the forked element 200 is properly aligned with the bone plate 12.

What is claimed is:

1. An orthopedic fixation system comprising:
   a bone plate having a first plurality of apertures passing therethrough, each aperture of the first plurality of apertures adapted to receive a bone fastener, the first plurality of apertures formed along the bone plate between a first end and a second end of the bone plate;
   a targeting arm having a second plurality of apertures passing therethrough and formed along the targeting arm from a first end to a second end of the targeting arm, each of the second plurality of apertures configured and arranged for targeting of the bone fastener to a select one of the first plurality of apertures, an imaginary targeting line extending from a first aperture of the first plurality of apertures at the first end of the bone plate to a first aperture of the second plurality of apertures at the first end of the targeting arm; and
   a mounting member for mounting the targeting arm relative to the bone plate, the mounting member including:
      a first end configured to be secured to the first end of the bone plate and a second end secured to the first end of the targeting arm, the first end including a forked element having first and second members positioned on laterally opposing sides of the first aperture of the first plurality of apertures such that the first aperture of the first plurality of apertures is positioned between the first and second members;
      a housing coupled near the first end of the mounting member and axially movable relative to the forked element to move the first and second members between a first position in which the first and second members are movable relative to the bone plate and a second position in which the first and second members are coupled to the bone plate, at least a portion of the forked element positioned inside the housing; and
      an actuation member coupled to the forked element and the housing, the actuation member rotatable relative to the forked element and the housing to move the housing relative to the forked element.

2. The system of claim 1, wherein the bone plate further comprises recessed location features, and the forked element includes mating features that engages the recessed location features to couple the first end of the mounting member to the bone plate.

3. The system of claim 1, wherein the bone plate further comprises a bow radius that is adapted to allow the bone plate to mate with the anatomy, and the targeting arm further comprises a corresponding bow radius.

4. The system of claim 1, wherein the second end of the mounting member further comprises at least one targeting arm locator that cooperates with at least one aperture defined through the targeting arm, and a bore that is adapted to receive a coupling knob to couple the targeting arm to the mounting member.

5. The system of claim 1, wherein the second end of the mounting member is offset from the first end of the mounting member to provide access to all of the plurality of apertures of the bone plate.

6. The system of claim 1, wherein the bone plate has a proximal end, and a distal end, and the mounting member is secured to the proximal end of the bone plate or the distal end of the bone plate based upon a length of the bone plate.

7. The system of claim 6, wherein the first aperture of the plurality of apertures is located at the proximal end of the bone plate and a second aperture of the plurality of apertures is located at the distal end of the bone plate, the system further comprising:
   a locking wire guide that is coupled to the second aperture of the plurality of apertures to provide a support for the targeting arm.

8. The system of claim 7, wherein each aperture of the first plurality of apertures includes a plurality of threads, and the locking wire guide includes a plurality of threads at a distal end to couple the locking wire guide to the plate.

9. The system of claim 1, wherein the second end of the mounting member is angularly offset from the first end such that the second end is spaced from the imaginary targeting line.

10. The system of claim 1, wherein the housing includes first and second axially extending members laterally opposed from each other and configured to cooperate with the first and second members of the forked element to move the first and second members of the forked element between the first and second positions.

11. An orthopedic fixation system comprising:
   a bone plate having a first plurality of apertures passing therethrough, each aperture of the first plurality of apertures adapted to receive a bone fastener;
   a targeting arm having a second plurality of apertures passing therethrough, each of the second plurality of apertures configured and arranged for targeting of the bone fastener to a select one of the first plurality of apertures; and
   a mounting member for mounting the targeting arm relative to the bone plate, the mounting member including:
      a first end including a forked element that is movable between a first position in which the forked element is movable relative to the bone plate and a second position in which the forked element is secured to the bone plate;
      a second end having a platform for supporting the targeting arm relative to the bone plate;
      a housing coupled near the first end of the mounting member and axially movable relative to the forked element to move the forked element between the first position and the second position, at least a portion of the forked element positioned inside the housing;
      an actuation member coupled to the forked element and the housing, the actuation member rotatable relative to the housing and the forked element to axially move the housing relative to the forked element between the first position and the second position.

12. The system of claim 11, wherein the forked element includes first and second members that are positionable on laterally opposing sides of one of the plurality of apertures and movable relative to each other to secure the bone plate to the mounting member in the second position.

13. The system of claim 12, wherein the housing is disposed between the actuation member and the forked element, the housing movable by the actuation member to draw the first and second member towards each other to secure the bone plate in the second position.

14. The system of claim 13, wherein the housing comprises a first member and a second member laterally opposed from the first member that are movable to contact the first member and the second member of the forked element, respectively.

15. The system of claim 14, wherein the actuation member is rotatable relative to the forked member to linearly translate the first member and second member of the housing into contact with the first member and second member of the forked element to couple the mounting member to the bone plate in the second position.

16. The system of claim 15, wherein a plurality of threads are defined about the mounting member between the forked element and the second end of the mounting member, and the actuation member further comprises a plurality of threads that threadably engage the plurality of threads of the mounting member to enable the actuation member to rotate relative to the forked element.

17. The system of claim 16, wherein the mounting member further comprises a slot defined through the mounting member between the plurality of threads and the forked element for receipt of a pin coupled to the housing to constrain the motion of the housing relative to the forked element.

18. The system of claim 17, wherein the mounting member further comprises a central bore that extends from the first end to the second end, and a spring that is received into the central bore, adjacent to the pin, to bias the housing into the first position.

19. The system of claim 11, wherein the second end of the mounting member is angularly offset from the first end of the mounting member to provide access to each aperture of the first plurality of apertures when the first end is in the second position.

20. An orthopedic fixation system comprising:
 a bone plate having a first plurality of apertures passing therethrough, each aperture of the first plurality of apertures adapted to receive a bone fastener, the first plurality of apertures formed along the bone plate between a first end and a second end of the bone plate;
 a targeting arm having a second plurality of apertures passing therethrough and formed along the targeting arm between a first end and a second end of the targeting arm, each of the second plurality of apertures configured and arranged for targeting of the bone fastener to a select one of first plurality of apertures, an imaginary targeting line extending from a first aperture of the first plurality of apertures at the first end of the bone plate to a first aperture of the second plurality of apertures at the first end of the targeting arm;
 a mounting member for mounting the targeting arm relative to the bone plate, the mounting member including:
  a first end having a housing and a forked element having first and second opposed members for engaging the bone plate, the housing axially movable relative to the forked element to secure the forked element to the bone plate, the housing including first and second axially extending members laterally opposed from each other, at least a portion of the forked element positioned inside the housing;
  a second end having a platform for supporting the targeting arm relative to the bone plate; and
  an actuation member coupled to the housing and rotatably coupled to the mounting member between the platform and the forked member, the actuation member rotatable to axially move the housing relative to the forked element such that the first and second members of the housing engage the first and second members of the forked element to secure the mounting member to the bone plate.

21. The system of claim 20, wherein the bone plate further comprises a proximal end that is bent to the right or to the left relative to a longitudinal axis of the bone plate to configure the bone plate to mate with the anatomy.

22. The system of claim 21, wherein the targeting arm further comprises a first side in which the second plurality of apertures correspond with the bone plate having the proximal end bent to the right and a second side in which the second plurality of apertures correspond with the bone plate having the proximal end bent to the left.

23. The system of claim 20, wherein the second end of the mounting member is angularly offset from the first end of the mounting member such that the second end is spaced from the imaginary targeting line.

24. The system of claim 20, wherein the housing defines an internal through passage, and wherein at least the portion of the first and second members of the forked element are movably positioned in the internal through passage.

* * * * *